(12) United States Patent
Ruijtenbeek et al.

(10) Patent No.: US 9,128,087 B2
(45) Date of Patent: Sep. 8, 2015

(54) NUCLEAR RECEPTOR ASSAY

(75) Inventors: Robby Ruijtenbeek, Utrecht (NL);
René Houtman, Culemborg (NL);
Marinus Gerardus Johannes Van Beuningen, Oss (NL)

(73) Assignee: PamGene B.V., Den Bosch (NL)

(*) Notice: Subject to any disclaimer, the term of this patent is extended or adjusted under 35 U.S.C. 154(b) by 1542 days.

(21) Appl. No.: 12/309,716

(22) PCT Filed: Sep. 10, 2007

(86) PCT No.: PCT/EP2007/059476
§ 371 (c)(1),
(2), (4) Date: Jan. 27, 2009

(87) PCT Pub. No.: WO2008/028978
PCT Pub. Date: Mar. 13, 2008

(65) Prior Publication Data
US 2009/0203537 A1    Aug. 13, 2009

(30) Foreign Application Priority Data
Sep. 8, 2006 (EP) .................................. 06447106

(51) Int. Cl.
*G01N 33/566* (2006.01)
*C40B 30/04* (2006.01)

(52) U.S. Cl.
CPC ............... *G01N 33/566* (2013.01); *C40B 30/04* (2013.01); *G01N 2333/70567* (2013.01); *G01N 2333/723* (2013.01); *G01N 2500/02* (2013.01)

(58) Field of Classification Search
None
See application file for complete search history.

(56) References Cited

U.S. PATENT DOCUMENTS 6,410,245 B1    6/2002    Northrop et al.
(Continued)

FOREIGN PATENT DOCUMENTS

| WO | 99/50664 A1 | 10/1999 |
| WO | 99/59664 A1 | 11/1999 |
| WO | WO 2005/054501 | * 6/2005 |

OTHER PUBLICATIONS

Flores et al. (Isolation and Functional Analysis of a Keratinocyte-Derived, Ligand-Regulated Nuclear Receptor Comodulator, 2004, Journal of Investigative Dermatology, vol. 123, pp. 1092-1101).*

Inglese et al. (Quantitative high-throughput screening: a titration-based approach that efficiently identifies biological activities in large chemical libraries, Aug. 1, 2006, PNAS, vol. 103, pp. 11473-11478).*

(Continued)

*Primary Examiner* — Samuel Woolwine
*Assistant Examiner* — Kaijiang Zhang
(74) *Attorney, Agent, or Firm* — Amster, Rothstein & Ebenstein LLP

(57) ABSTRACT

The present invention relates to methods for measuring compound efficacy and potency on nuclear receptor-co-regulator interaction, comprising the steps of (a) co-incubating at least one nuclear receptor and at least one compound under conditions that allow interaction; (b) co-incubating the nuclear receptor-compound mixture of step (a) with an array of co-regulators, under conditions that allow compound modulated receptor-co-regulator interaction; (c) determination of compound-modulated receptor-co-regulator interaction in function B of co-regulator concentration, and (d) determination of compound-modulated receptor-co-regulator interaction in function of compound concentration; wherein steps (c) and (d) are performed in a single assay.

12 Claims, 9 Drawing Sheets

(56) References Cited

U.S. PATENT DOCUMENTS

2003/0039980 A1* 2/2003 Thompson .................. 435/6
2005/0202440 A1 9/2005 Fletterick et al.
2006/0110732 A1* 5/2006 Bone et al. .................. 435/6

OTHER PUBLICATIONS

The Search Report for PCT Application No. PCT/EP2007/059476, as published under WO 2008/028978 A1.
The International Preliminary Reort for PCT Application No. PCT/EP2007/059476.

* cited by examiner

SEQUENCE LISTING

```
<160> NUMBER OF SEQ ID NOS: 84

<210> SEQ ID NO 1
<211> LENGTH: 23
<212> TYPE: PRT
<213> ORGANISM: Homo sapiens

<400> SEQUENCE: 1

Ser Val Gln Pro Pro Arg Ser Ile Ser Pro Ser Ala Leu Gln Asp Leu
1               5                   10                  15

Leu Arg Thr Leu Lys Ser Pro
            20
```

```
<210> SEQ ID NO 2
<211> LENGTH: 24
<212> TYPE: PRT
<213> ORGANISM: Homo sapiens

<400> SEQUENCE: 2

Thr Ala Asp Pro Glu Lys Arg Lys Leu Ile Gln Gln Gln Leu Val Leu
1               5                   10                  15

Leu Leu His Ala His Lys Cys Gln
            20

<210> SEQ ID NO 3
<211> LENGTH: 24
<212> TYPE: PRT
<213> ORGANISM: Homo sapiens

<400> SEQUENCE: 3

Thr Ala Asp Pro Glu Lys Arg Lys Leu Ile Gln Gln Gln Leu Val Leu
1               5                   10                  15

Leu Leu His Ala His Lys Ser Gln
            20

<210> SEQ ID NO 4
<211> LENGTH: 24
<212> TYPE: PRT
<213> ORGANISM: Homo sapiens

<400> SEQUENCE: 4

Gly Asn Leu Val Pro Asp Ala Ala Ser Lys His Lys Gln Leu Ser Glu
1               5                   10                  15

Leu Leu Arg Gly Gly Ser Gly Ser
            20

<210> SEQ ID NO 5
<211> LENGTH: 24
<212> TYPE: PRT
<213> ORGANISM: Homo sapiens

<400> SEQUENCE: 5

Gly Glu Asp His Pro Arg Gln Gly Ser Ile Leu Tyr Ser Leu Leu Thr
1               5                   10                  15

Ser Ser Lys Gln Thr His Val Ala
            20

<210> SEQ ID NO 6
<211> LENGTH: 23
<212> TYPE: PRT
<213> ORGANISM: Homo sapiens

<400> SEQUENCE: 6

Met Ala Gly Glu Asn His Gln Trp Gln Gly Ser Ile Leu Tyr Asn Met
1               5                   10                  15

Leu Met Ser Ala Lys Gln Thr
            20

<210> SEQ ID NO 7
<211> LENGTH: 23
<212> TYPE: PRT
<213> ORGANISM: Homo sapiens

<400> SEQUENCE: 7

Phe Ser Gly Lys Asp His Pro Arg Gln Gly Ser Ile Leu Tyr Ser Met
1               5                   10                  15
```

Leu Thr Ser Ala Lys Gln Thr
            20

<210> SEQ ID NO 8
<211> LENGTH: 23
<212> TYPE: PRT
<213> ORGANISM: Homo sapiens

<400> SEQUENCE: 8

Ser Pro Leu Lys Pro Gly Thr Val Ser Gln Gln Ala Leu Gln Asn Leu
1               5                   10                  15

Leu Arg Thr Leu Arg Ser Pro
            20

<210> SEQ ID NO 9
<211> LENGTH: 23
<212> TYPE: PRT
<213> ORGANISM: Homo sapiens

<400> SEQUENCE: 9

Gly Met Val Gln Asp Ala Ala Ser Lys His Lys Gln Leu Ser Glu Leu
1               5                   10                  15

Leu Arg Ser Gly Ser Ser Pro
            20

<210> SEQ ID NO 10
<211> LENGTH: 23
<212> TYPE: PRT
<213> ORGANISM: Homo sapiens

<400> SEQUENCE: 10

Pro Leu Gly Ser Ala Met Leu Arg Pro Asn Pro Ile Leu Ala Arg Leu
1               5                   10                  15

Leu Arg Ala His Gly Ala Pro
            20

<210> SEQ ID NO 11
<211> LENGTH: 23
<212> TYPE: PRT
<213> ORGANISM: Homo sapiens

<400> SEQUENCE: 11

Leu His Leu Ala Val Ile His Gln His Glu Pro Phe Leu Asp Phe Leu
1               5                   10                  15

Leu Gly Phe Ser Ala Gly Thr
            20

<210> SEQ ID NO 12
<211> LENGTH: 23
<212> TYPE: PRT
<213> ORGANISM: Homo sapiens

<400> SEQUENCE: 12

Pro Leu Val Ser Gln Asn Asn Glu Gln Gly Ser Thr Leu Arg Asp Leu
1               5                   10                  15

Leu Thr Thr Thr Ala Gly Lys
            20

<210> SEQ ID NO 13
<211> LENGTH: 23
<212> TYPE: PRT
<213> ORGANISM: Homo sapiens

```
<400> SEQUENCE: 13

Gln Trp Val Ser Ser Leu Asn Glu Arg Glu Gln Glu Leu His Asn Leu
1               5                   10                  15

Leu Glu Val Val Ser Gln Ser
            20

<210> SEQ ID NO 14
<211> LENGTH: 21
<212> TYPE: PRT
<213> ORGANISM: Homo sapiens

<400> SEQUENCE: 14

Thr Ser Gly Pro Gln Thr Pro Gln Ala Gln Gln Lys Ser Leu Leu Gln
1               5                   10                  15

Gln Leu Leu Thr Glu
            20

<210> SEQ ID NO 15
<211> LENGTH: 24
<212> TYPE: PRT
<213> ORGANISM: Homo sapiens

<400> SEQUENCE: 15

Ser Asp Gly Asp Ser Lys Tyr Ser Gln Thr Ser His Lys Leu Val Gln
1               5                   10                  15

Leu Leu Thr Thr Thr Ala Glu Gln
            20

<210> SEQ ID NO 16
<211> LENGTH: 24
<212> TYPE: PRT
<213> ORGANISM: Homo sapiens

<400> SEQUENCE: 16

Pro Ser Ser His Ser Ser Leu Thr Glu Arg His Lys Ile Leu His Arg
1               5                   10                  15

Leu Leu Gln Glu Gly Ser Pro Ser
            20

<210> SEQ ID NO 17
<211> LENGTH: 23
<212> TYPE: PRT
<213> ORGANISM: Homo sapiens

<400> SEQUENCE: 17

Ala Ser Lys Lys Lys Glu Ser Lys Asp His Gln Leu Leu Arg Tyr Leu
1               5                   10                  15

Leu Asp Lys Asp Glu Lys Asp
            20

<210> SEQ ID NO 18
<211> LENGTH: 24
<212> TYPE: PRT
<213> ORGANISM: Homo sapiens

<400> SEQUENCE: 18

Gly Gln Ser Arg Leu His Asp Ser Lys Gly Gln Thr Lys Leu Leu Gln
1               5                   10                  15

Leu Leu Thr Thr Lys Ser Asp Gln
            20
```

<210> SEQ ID NO 19
<211> LENGTH: 24
<212> TYPE: PRT
<213> ORGANISM: Homo sapiens

<400> SEQUENCE: 19

Ser Thr His Gly Thr Ser Leu Lys Glu Lys His Lys Ile Leu His Arg
1               5                   10                  15

Leu Leu Gln Asp Ser Ser Ser Pro
            20

<210> SEQ ID NO 20
<211> LENGTH: 23
<212> TYPE: PRT
<213> ORGANISM: Homo sapiens

<400> SEQUENCE: 20

Glu Pro Val Ser Pro Lys Lys Glu Asn Ala Leu Leu Arg Tyr Leu
1               5                   10                  15

Leu Asp Lys Asp Asp Thr Lys
            20

<210> SEQ ID NO 21
<211> LENGTH: 23
<212> TYPE: PRT
<213> ORGANISM: Homo sapiens

<400> SEQUENCE: 21

Ser Gln Ser Thr Phe Asn Asn Pro Arg Pro Gly Gln Leu Gly Arg Leu
1               5                   10                  15

Leu Pro Asn Gln Asn Leu Pro
            20

<210> SEQ ID NO 22
<211> LENGTH: 23
<212> TYPE: PRT
<213> ORGANISM: Homo sapiens

<400> SEQUENCE: 22

Lys Lys Lys Gly Gln Gly Val Ile Asp Lys Asp Ser Leu Gly Pro Leu
1               5                   10                  15

Leu Leu Gln Ala Leu Asp Gly
            20

<210> SEQ ID NO 23
<211> LENGTH: 23
<212> TYPE: PRT
<213> ORGANISM: Homo sapiens

<400> SEQUENCE: 23

Gln Arg Gly Pro Leu Glu Ser Lys Gly His Lys Lys Leu Leu Gln Leu
1               5                   10                  15

Leu Thr Cys Ser Ser Asp Asp
            20

<210> SEQ ID NO 24
<211> LENGTH: 23
<212> TYPE: PRT
<213> ORGANISM: Homo sapiens

<400> SEQUENCE: 24

Gln Arg Gly Pro Leu Glu Ser Lys Gly His Lys Lys Leu Leu Gln Leu

-continued

```
1               5                   10                  15

Leu Thr Ser Ser Ser Asp Asp
            20

<210> SEQ ID NO 25
<211> LENGTH: 23
<212> TYPE: PRT
<213> ORGANISM: Homo sapiens

<400> SEQUENCE: 25

Met His Gly Ser Leu Leu Gln Glu Lys His Arg Ile Leu His Lys Leu
1               5                   10                  15

Leu Gln Asn Gly Asn Ser Pro
            20

<210> SEQ ID NO 26
<211> LENGTH: 23
<212> TYPE: PRT
<213> ORGANISM: Homo sapiens

<400> SEQUENCE: 26

His Gly Ser Gln Asn Arg Pro Leu Leu Arg Asn Ser Leu Asp Asp Leu
1               5                   10                  15

Leu Gly Pro Pro Ser Asn Ala
            20

<210> SEQ ID NO 27
<211> LENGTH: 23
<212> TYPE: PRT
<213> ORGANISM: Homo sapiens

<400> SEQUENCE: 27

Leu Val Ser Pro Ala Met Arg Glu Ala Pro Thr Ser Leu Ser Gln Leu
1               5                   10                  15

Leu Asp Asn Ser Gly Ala Pro
            20

<210> SEQ ID NO 28
<211> LENGTH: 23
<212> TYPE: PRT
<213> ORGANISM: Homo sapiens

<400> SEQUENCE: 28

Pro Val Asn Lys Asp Val Thr Leu Thr Ser Pro Leu Leu Val Asn Leu
1               5                   10                  15

Leu Gln Ser Asp Ile Ser Ala
            20

<210> SEQ ID NO 29
<211> LENGTH: 23
<212> TYPE: PRT
<213> ORGANISM: Homo sapiens

<400> SEQUENCE: 29

Met Gly Gln Val Pro Arg Thr His Arg Leu Ile Thr Leu Ala Asp His
1               5                   10                  15

Ile Cys Gln Ile Ile Thr Gln
            20

<210> SEQ ID NO 30
<211> LENGTH: 23
<212> TYPE: PRT
```

<213> ORGANISM: Homo sapiens

<400> SEQUENCE: 30

Met Gly Gln Val Pro Arg Thr His Arg Leu Ile Thr Leu Ala Asp His
1               5                   10                  15

Ile Ser Gln Ile Ile Thr Gln
            20

<210> SEQ ID NO 31
<211> LENGTH: 23
<212> TYPE: PRT
<213> ORGANISM: Homo sapiens

<400> SEQUENCE: 31

Gly His Ser Phe Ala Asp Pro Ala Ser Asn Leu Gly Leu Glu Asp Ile
1               5                   10                  15

Ile Arg Lys Ala Leu Met Gly
            20

<210> SEQ ID NO 32
<211> LENGTH: 23
<212> TYPE: PRT
<213> ORGANISM: Homo sapiens

<400> SEQUENCE: 32

Ala Pro Gly Val Lys Gly His Gln Arg Val Val Thr Leu Ala Gln His
1               5                   10                  15

Ile Ser Glu Val Ile Thr Gln
            20

<210> SEQ ID NO 33
<211> LENGTH: 23
<212> TYPE: PRT
<213> ORGANISM: Homo sapiens

<400> SEQUENCE: 33

Gln Ala Val Gln Glu His Ala Ser Thr Asn Met Gly Leu Glu Ala Ile
1               5                   10                  15

Ile Arg Lys Ala Leu Met Gly
            20

<210> SEQ ID NO 34
<211> LENGTH: 23
<212> TYPE: PRT
<213> ORGANISM: Homo sapiens

<400> SEQUENCE: 34

Asp Ser Val Arg Lys Gly Lys Gln Asp Ser Thr Leu Leu Ala Ser Leu
1               5                   10                  15

Leu Gln Ser Phe Ser Ser Arg
            20

<210> SEQ ID NO 35
<211> LENGTH: 23
<212> TYPE: PRT
<213> ORGANISM: Homo sapiens

<400> SEQUENCE: 35

Lys Asp Leu Arg Cys Tyr Gly Val Ala Ser Ser His Leu Lys Thr Leu
1               5                   10                  15

Leu Lys Lys Ser Lys Val Lys
            20

<210> SEQ ID NO 36
<211> LENGTH: 23
<212> TYPE: PRT
<213> ORGANISM: Homo sapiens

<400> SEQUENCE: 36

Lys Asp Leu Arg Ser Tyr Gly Val Ala Ser Ser His Leu Lys Thr Leu
1               5                   10                  15

Leu Lys Lys Ser Lys Val Lys
            20

<210> SEQ ID NO 37
<211> LENGTH: 23
<212> TYPE: PRT
<213> ORGANISM: Homo sapiens

<400> SEQUENCE: 37

Arg Asn Asn Ile Lys Gln Ala Ala Asn Ser Leu Leu Leu His Leu
1               5                   10                  15

Leu Lys Ser Gln Thr Ile Pro
            20

<210> SEQ ID NO 38
<211> LENGTH: 23
<212> TYPE: PRT
<213> ORGANISM: Homo sapiens

<400> SEQUENCE: 38

Lys Asn Ser Lys Leu Asn Ser His Gln Lys Val Thr Leu Leu Gln Leu
1               5                   10                  15

Leu Leu Gly His Lys Asn Glu
            20

<210> SEQ ID NO 39
<211> LENGTH: 23
<212> TYPE: PRT
<213> ORGANISM: Homo sapiens

<400> SEQUENCE: 39

Ser Glu Ile Glu Asn Leu Leu Glu Arg Arg Thr Val Leu Gln Leu Leu
1               5                   10                  15

Leu Gly Asn Pro Thr Lys Gly
            20

<210> SEQ ID NO 40
<211> LENGTH: 27
<212> TYPE: PRT
<213> ORGANISM: Homo sapiens

<400> SEQUENCE: 40

Pro Val Ser Pro Gln Asp Phe Ser Phe Ser Lys Asn Gly Leu Leu Ser
1               5                   10                  15

Arg Leu Leu Arg Gln Asn Gln Asp Ser Tyr Leu
            20                  25

<210> SEQ ID NO 41
<211> LENGTH: 23
<212> TYPE: PRT
<213> ORGANISM: Homo sapiens

<400> SEQUENCE: 41

-continued

Arg Ser Trp Ala Arg Glu Ser Lys Ser Phe Asn Val Leu Lys Gln Leu
1               5                   10                  15

Leu Leu Ser Glu Asn Cys Val
            20

<210> SEQ ID NO 42
<211> LENGTH: 23
<212> TYPE: PRT
<213> ORGANISM: Homo sapiens

<400> SEQUENCE: 42

Arg Ser Trp Ala Arg Glu Ser Lys Ser Phe Asn Val Leu Lys Gln Leu
1               5                   10                  15

Leu Leu Ser Glu Asn Ser Val
            20

<210> SEQ ID NO 43
<211> LENGTH: 23
<212> TYPE: PRT
<213> ORGANISM: Homo sapiens

<400> SEQUENCE: 43

Glu Glu Asp Ala Asp Thr Lys Gln Val Tyr Phe Tyr Leu Phe Lys Leu
1               5                   10                  15

Leu Arg Lys Ser Ile Leu Gln
            20

<210> SEQ ID NO 44
<211> LENGTH: 24
<212> TYPE: PRT
<213> ORGANISM: Homo sapiens

<400> SEQUENCE: 44

His Gly Glu Asp Phe Ser Lys Val Ser Gln Asn Pro Ile Leu Thr Ser
1               5                   10                  15

Leu Leu Gln Ile Thr Gly Asn Gly
            20

<210> SEQ ID NO 45
<211> LENGTH: 24
<212> TYPE: PRT
<213> ORGANISM: Homo sapiens

<400> SEQUENCE: 45

Val Ser Ser Met Ala Gly Asn Thr Lys Asn His Pro Met Leu Met Asn
1               5                   10                  15

Leu Leu Lys Asp Asn Pro Ala Gln
            20

<210> SEQ ID NO 46
<211> LENGTH: 26
<212> TYPE: PRT
<213> ORGANISM: Homo sapiens

<400> SEQUENCE: 46

Asp Gly Thr Pro Pro Gln Glu Ala Glu Glu Pro Ser Leu Leu Lys
1               5                   10                  15

Lys Leu Leu Leu Ala Pro Ala Asn Thr Gln
            20                  25

<210> SEQ ID NO 47
<211> LENGTH: 21

```
<212> TYPE: PRT
<213> ORGANISM: Homo sapiens

<400> SEQUENCE: 47

Pro Pro Gln Glu Ala Glu Pro Ser Leu Leu Lys Lys Leu Leu Leu
1               5                   10                  15

Ala Pro Ala Asn Thr
            20

<210> SEQ ID NO 48
<211> LENGTH: 21
<212> TYPE: PRT
<213> ORGANISM: Homo sapiens

<400> SEQUENCE: 48

Pro Ala Pro Glu Val Asp Glu Leu Ser Leu Leu Gln Lys Leu Leu
1               5                   10                  15

Ala Thr Ser Tyr Pro
            20

<210> SEQ ID NO 49
<211> LENGTH: 21
<212> TYPE: PRT
<213> ORGANISM: Homo sapiens

<400> SEQUENCE: 49

Ala Glu Phe Ser Ile Leu Arg Glu Leu Leu Ala Gln Asp Val Leu Cys
1               5                   10                  15

Asp Val Ser Lys Pro
            20

<210> SEQ ID NO 50
<211> LENGTH: 23
<212> TYPE: PRT
<213> ORGANISM: Homo sapiens

<400> SEQUENCE: 50

Thr Phe Glu Val Ala Glu Ala Pro Val Pro Ser Ile Leu Lys Lys Ile
1               5                   10                  15

Leu Leu Glu Glu Pro Ser Ser
            20

<210> SEQ ID NO 51
<211> LENGTH: 23
<212> TYPE: PRT
<213> ORGANISM: Homo sapiens

<400> SEQUENCE: 51

Ser Pro Ser Gln Gly Ala Ala Ser Arg Pro Ala Ile Leu Tyr Ala Leu
1               5                   10                  15

Leu Ser Ser Ser Leu Lys Ala
            20

<210> SEQ ID NO 52
<211> LENGTH: 23
<212> TYPE: PRT
<213> ORGANISM: Homo sapiens

<400> SEQUENCE: 52

Phe Val Asn Leu Tyr Thr Arg Glu Arg Gln Asp Arg Leu Ala Val Leu
1               5                   10                  15

Leu Pro Gly Arg His Pro Ser
```

<210> SEQ ID NO 53
<211> LENGTH: 23
<212> TYPE: PRT
<213> ORGANISM: Homo sapiens

<400> SEQUENCE: 53

Leu Gln Asn Leu Lys Asn Leu Gly Glu Ser Ala Thr Leu Arg Ser Leu
1               5                   10                  15

Leu Leu Asn Pro His Leu Arg
            20

<210> SEQ ID NO 54
<211> LENGTH: 14
<212> TYPE: PRT
<213> ORGANISM: Homo sapiens

<400> SEQUENCE: 54

Gln Leu Arg Leu Gln Leu Gln Gln Arg Leu Gln Gly Gln Gln
1               5                   10

<210> SEQ ID NO 55
<211> LENGTH: 14
<212> TYPE: PRT
<213> ORGANISM: Homo sapiens

<400> SEQUENCE: 55

Gln Pro Pro Leu Asn Ala Gln Met Leu Ala Gln Arg Gln Arg
1               5                   10

<210> SEQ ID NO 56
<211> LENGTH: 14
<212> TYPE: PRT
<213> ORGANISM: Homo sapiens

<400> SEQUENCE: 56

Pro Gln Gly Ala Pro Gln Gln Phe Pro Tyr Pro Pro Asn Tyr
1               5                   10

<210> SEQ ID NO 57
<211> LENGTH: 14
<212> TYPE: PRT
<213> ORGANISM: Homo sapiens

<400> SEQUENCE: 57

Gln Leu Arg Leu Gln Leu Gln His Arg Leu Gln Ala Gln Gln
1               5                   10

<210> SEQ ID NO 58
<211> LENGTH: 14
<212> TYPE: PRT
<213> ORGANISM: Homo sapiens

<400> SEQUENCE: 58

Gln Ala Pro Ile Asn Ala Gln Met Leu Ala Gln Arg Gln Arg
1               5                   10

<210> SEQ ID NO 59
<211> LENGTH: 14
<212> TYPE: PRT
<213> ORGANISM: Homo sapiens

<400> SEQUENCE: 59

Pro Gln Ala Asn Ala Gln Gln Phe Pro Phe Pro Pro Asn Tyr
1               5                   10

<210> SEQ ID NO 60
<211> LENGTH: 14
<212> TYPE: PRT
<213> ORGANISM: Homo sapiens

<400> SEQUENCE: 60

Gln Leu Arg Met Gln Leu Gln Gln Arg Leu Gln Gly Gln Gln
1               5                   10

<210> SEQ ID NO 61
<211> LENGTH: 14
<212> TYPE: PRT
<213> ORGANISM: Homo sapiens

<400> SEQUENCE: 61

Gln Gly Phe Leu Asn Ala Gln Met Val Ala Gln Arg Ser Arg
1               5                   10

<210> SEQ ID NO 62
<211> LENGTH: 17
<212> TYPE: PRT
<213> ORGANISM: Homo sapiens

<400> SEQUENCE: 62

Lys Thr Tyr Arg Gly Ala Phe Gln Asn Leu Phe Gln Ser Val Arg Glu
1               5                   10                  15
Gly

<210> SEQ ID NO 63
<211> LENGTH: 17
<212> TYPE: PRT
<213> ORGANISM: Homo sapiens

<400> SEQUENCE: 63

Gly Gly Glu Thr Pro Leu Phe Lys Gln Phe Phe Lys Asn Trp Arg Asp
1               5                   10                  15
Gly

<210> SEQ ID NO 64
<211> LENGTH: 16
<212> TYPE: PRT
<213> ORGANISM: Homo sapiens

<400> SEQUENCE: 64

Pro Gln Ala Gln Gln Lys Ser Leu Leu Gln Gln Leu Leu Thr Glu Gly
1               5                   10                  15

<210> SEQ ID NO 65
<211> LENGTH: 17
<212> TYPE: PRT
<213> ORGANISM: Homo sapiens

<400> SEQUENCE: 65

Ser Lys Gly Gln Thr Lys Leu Leu Gln Leu Leu Thr Thr Lys Ser Asp
1               5                   10                  15
Gly

<210> SEQ ID NO 66
<211> LENGTH: 17
<212> TYPE: PRT

-continued

<213> ORGANISM: Homo sapiens

<400> SEQUENCE: 66

Lys Glu Asn Asn Ala Leu Leu Arg Tyr Leu Leu Asp Arg Asp Asp Pro
1               5                   10                  15

Gly

<210> SEQ ID NO 67
<211> LENGTH: 17
<212> TYPE: PRT
<213> ORGANISM: Homo sapiens

<400> SEQUENCE: 67

Arg Glu Thr Ser Glu Lys Phe Lys Leu Leu Phe Gln Ser Tyr Asn Val
1               5                   10                  15

Gly

<210> SEQ ID NO 68
<211> LENGTH: 17
<212> TYPE: PRT
<213> ORGANISM: Homo sapiens

<400> SEQUENCE: 68

Ser Leu Lys Arg Arg Leu Phe Arg Ser Met Phe Leu Ser Thr Ala Ala
1               5                   10                  15

Gly

<210> SEQ ID NO 69
<211> LENGTH: 17
<212> TYPE: PRT
<213> ORGANISM: Homo sapiens

<400> SEQUENCE: 69

Thr Pro Pro Pro Lys Lys Phe Arg Ser Leu Phe Phe Gly Ser Ile Leu
1               5                   10                  15

Gly

<210> SEQ ID NO 70
<211> LENGTH: 17
<212> TYPE: PRT
<213> ORGANISM: Homo sapiens

<400> SEQUENCE: 70

Met Met Asn Pro Leu Thr Phe Lys Glu Ile Phe Gln Thr Thr Val Pro
1               5                   10                  15

Gly

<210> SEQ ID NO 71
<211> LENGTH: 17
<212> TYPE: PRT
<213> ORGANISM: Homo sapiens

<400> SEQUENCE: 71

Lys Thr Tyr Arg Gly Ala Phe Gln Asn Phe Phe Gln Ser Val Arg Glu
1               5                   10                  15

Gly

<210> SEQ ID NO 72
<211> LENGTH: 17
<212> TYPE: PRT

```
<400> SEQUENCE: 72

Lys Thr Tyr Arg Gly Ala Phe Gln Asn Met Phe Gln Ser Val Arg Glu
1               5                   10                  15

Gly

<210> SEQ ID NO 73
<211> LENGTH: 17
<212> TYPE: PRT
<213> ORGANISM: Homo sapiens

<400> SEQUENCE: 73

Lys Thr Tyr Arg Gly Ala Phe Gln Asn Tyr Phe Gln Ser Val Arg Glu
1               5                   10                  15

Gly

<210> SEQ ID NO 74
<211> LENGTH: 17
<212> TYPE: PRT
<213> ORGANISM: Homo sapiens

<400> SEQUENCE: 74

Lys Thr Tyr Arg Gly Ala Leu Gln Asn Leu Leu Gln Ser Val Arg Glu
1               5                   10                  15

Gly

<210> SEQ ID NO 75
<211> LENGTH: 17
<212> TYPE: PRT
<213> ORGANISM: Homo sapiens

<400> SEQUENCE: 75

Gly Gly Glu Thr Pro Ala Ala Lys Gln Phe Phe Lys Asn Trp Arg Asp
1               5                   10                  15

Gly

<210> SEQ ID NO 76
<211> LENGTH: 17
<212> TYPE: PRT
<213> ORGANISM: Homo sapiens

<400> SEQUENCE: 76

Gly Gly Glu Thr Pro Leu Phe Lys Gln Ala Ala Lys Asn Trp Arg Asp
1               5                   10                  15

Gly

<210> SEQ ID NO 77
<211> LENGTH: 17
<212> TYPE: PRT
<213> ORGANISM: Homo sapiens

<400> SEQUENCE: 77

Gly Gly Glu Thr Pro Leu Phe Ala Ala Phe Phe Lys Asn Trp Arg Asp
1               5                   10                  15

Gly

<210> SEQ ID NO 78
<211> LENGTH: 17
<212> TYPE: PRT
<213> ORGANISM: Homo sapiens
```

<400> SEQUENCE: 78

Gly Gly Glu Thr Pro Leu Phe Lys Gln Phe Phe Ala Ala Trp Arg Asp
1               5                   10                  15

Gly

<210> SEQ ID NO 79
<211> LENGTH: 17
<212> TYPE: PRT
<213> ORGANISM: Homo sapiens

<400> SEQUENCE: 79

Gly Gly Glu Ala Ala Leu Phe Lys Gln Phe Phe Lys Asn Trp Arg Asp
1               5                   10                  15

Gly

<210> SEQ ID NO 80
<211> LENGTH: 17
<212> TYPE: PRT
<213> ORGANISM: Homo sapiens

<400> SEQUENCE: 80

Gly Gly Glu Thr Pro Leu Phe Lys Gln Leu Phe Lys Asn Trp Arg Asp
1               5                   10                  15

Gly

<210> SEQ ID NO 81
<211> LENGTH: 17
<212> TYPE: PRT
<213> ORGANISM: Homo sapiens

<400> SEQUENCE: 81

Gly Gly Glu Thr Pro Leu Phe Lys Gln Met Phe Lys Asn Trp Arg Asp
1               5                   10                  15

Gly

<210> SEQ ID NO 82
<211> LENGTH: 17
<212> TYPE: PRT
<213> ORGANISM: Homo sapiens

<400> SEQUENCE: 82

Gly Gly Glu Thr Pro Leu Phe Lys Gln Tyr Phe Lys Asn Trp Arg Asp
1               5                   10                  15

Gly

<210> SEQ ID NO 83
<211> LENGTH: 17
<212> TYPE: PRT
<213> ORGANISM: Homo sapiens

<400> SEQUENCE: 83

Gly Gly Glu Thr Pro Leu Phe Lys Gln Phe Phe Lys Asn Trp Arg Asp
1               5                   10                  15

Gly

<210> SEQ ID NO 84
<211> LENGTH: 13
<212> TYPE: PRT
<213> ORGANISM: Artificial Sequence
<220> FEATURE:
<223> OTHER INFORMATION: NCOA1-derived peptoid A

```
-continued

<220> FEATURE:
<221> NAME/KEY: MISC_FEATURE
<222> LOCATION: (11)..(11)
<223> OTHER INFORMATION: X = nL

<400> SEQUENCE: 84

Glu Arg Lys His Lys Ile Leu His Arg Leu Xaa Gln Glu
1               5                   10
```

NUCLEAR RECEPTOR ASSAY

This is a U.S. national phase of PCT Application No. PCT/EP2007/059476, filed Sep. 10, 2007, which claims the benefit of European Application No. 06447106.3, filed Sep. 8, 2006.

FIELD OF THE INVENTION

The present invention relates to assaying interactions between nuclear receptors and co-regulators. In particular, the present invention relates to high throughput screening of compounds and measurement of their effect on nuclear hormone receptor-co-regulator binding events.

BACKGROUND

A variety of compounds may affect the rate at which existing biologic functions proceed. They are developed to speed up or slow down biological processes, e.g. by modulating enzyme activity or the binding of interacting molecules.

A compound's action is affected by the degree of attraction to its target (target affinity) and, once bound to the target, its ability to induce an effect (intrinsic activity or efficacy). Various compounds show various target affinity and efficacy.

Important classes of compounds functioning as modulator molecules are nuclear receptor interacting ligands.

The nuclear hormone receptor (further referred to as "nuclear receptor" or "NR") super family comprises approximately 50 members that play a role in a broad range of physiologic processes, including metabolism, homeostasis, and reproduction. The classical NR proteins contain a central DNA-binding domain (DBD), which binds the promoter region of target genes, and a COOH-terminal ligand-binding domain (LBD). One of the functions of the LBD is co-regulator recruitment. Ligand binding induces a conformational change of the LBD. Subsequent binding to a co-activator or co-repressor protein then results in NR transactivation or the switch between a transcriptionally inactive state and an activated state of the receptor. Depending on the nature of the co-regulator, being either a co-activator or -repressor, an initiation point for the gene transcription machinery is respectively formed or blocked, and the target gene is activated or silenced. In addition, activated nuclear receptors can also alter pathways in the cytoplasm, such as kinase phosphorylation cascades.

As NRs respond to small ligand molecules or compounds and correspond to potent regulators of cell function, life and death, they are particularly attractive targets for the design of novel therapeutic agents. Small molecular ligands include biogenic amines, amino acids, ions, lipids, nucleotides, and chemical compounds that represent the majority of classic drugs.

A critical step in the design process of a therapeutic compound is the elucidation of its function. In the context of nuclear receptor interactions this function can be deduced from the modulation of receptor affinity for a co-activator or co-repressor and the resulting effect such as the transcriptional activity of the NR.

Methods to measure compound effects on nuclear receptor affinity for a co-regulator are known in the art. For example, Zhou et al (Mol. Endo. 1998, Vol. 12 (10), p. 1594-1604) describes the characterization of NR affinities for co-activator-derived domains by fluorescence resonance energy transfer (FRET). With this method, the ligand potency, calculated as EC50, is determined by quantification of the binding at equilibrium between nuclear receptor and co-activator at multiple ligand concentrations. However the multiple data points needed (for each variation in NR, co-regulator, ligand and their respective concentration, a separate sample and measurement is needed) makes this method by Zhou et al rather cumbersome and time and sample consuming.

Alternative methods in the art are described e.g. by Iannone et al (Cytometry 2001, Vol. (44), p 326-337) relating to the characterization of ligand function by measuring NR-LBD binding to a set of fluorescent microsphere-immobilised peptides with an LxxLL motif (in which L represents leucine and x can be any amino acid) the minimal entity in co-regulator proteins for interaction with a NR. Interaction is measured at a saturating ligand concentration while receptor concentrations are varied in separate samples. From these data an apparent Kd (affinity) of the receptor for each peptide is calculated. Other known motifs include but are not limited to LxxML, FxxFF or LxxIL (in which F represents phenylalanine, M represents Methionine, I represents isoleucine and x can be any amino acid).

Iannone et al (Mol. Endo. 2004, Vol. (18), p 1064-1081) also described the clustering of a set of ligands based on their profile of enhancement and or decrease of NR binding to individual peptides using saturating ligand concentrations by applying the same method as described above.

Again by applying the same method as described above Iannone et al (Cytometry Part A, 2006, Vol. (69A), p 374-383) also assessed the apparent affinity (Kd) by varying the density of the immobilized LxxLL peptides using a single NR concentration.

Disadvantages of the methods known in the art is that in most assays, each variation in NR, co-regulator, ligand and their respective concentration to either determine compound potency or efficacy requires measurements in separate samples and separate assays. The ability to perform such studies are limited by time, costs, reproducibility and availability of the bio-molecules such as the NR proteins, which are often difficult to obtain in high purity at large quantities.

Further, compound efficacies are calculated from NR-co-regulator binding in absence and presence of ligand (at a saturating concentration). As such the dynamic range of the readout is limited by the fact the maximal binding is measured when either one of the free binding partners (NR or co-regulator) is depleted. This limits the discrimination of high-efficacy binding-enhancing ligands.

The present invention overcomes the above-mentioned disadvantages by providing a multiplex method allowing the determination of both a compound's potency and efficacy in a time and cost effective way. In particular, the present invention provides a multiplex method for the determination of the potency and efficacy of nuclear receptor ligands in function of a kinetic reading of receptor-co-regulator binding.

SUMMARY OF THE INVENTION

The present invention relates to methods for compound screening and measurement of their effect on receptor-co-regulator interaction.

In particular the present invention relates to a method for measuring compound efficacy and potency on nuclear receptor-co-regulator interaction, comprising the following steps:
  (i) co-incubating at least one nuclear receptor and at least one compound under conditions that allow interaction;
  (ii) co-incubating the nuclear receptor-compound mixture of step (i) with an array of co-regulators, under conditions that allow compound modulated receptor-co-regulator interaction;

(iii) determination of compound modulated receptor-co-regulator interaction in function of co-regulator concentration (iv) determination of compound modulated receptor-co-regulator interaction in function of compound concentration wherein steps (iii) and (iv) are performed in a single assay.

DESCRIPTION OF THE FIGURES

All SEQ ID NOs referred to in the following figure descriptions are listed in Table 1.

FIG. 1A shows the microarray layout with a set of 6 co-regulator-derived motifs X1 to X6 (X-axis), immobilized in a range of 10 concentrations Y1 to X10 (Y-axis) expressed in μM. FIG. 1B represents the top view of the first row of wells in a 96-well plate, showing the fluorescence results obtained for the induced ER interaction with a variety of peptides immobilized on each microarray as shown in FIG. 1A (each well has the same microarray) in the presence of estrogen concentrations varying from array to array. FIG. 1C shows the calculated binding curves of estrogen receptor alpha to the co-regulator derived peptide PGC1α (SEQ ID NO. 46). Each curve represents a single concentration of the estrogen (ligand). Each single curve is derived from a single sample (single estradiol concentration) applied to a single microarray. The X-axis represents the peptide concentration on the microarray expressed as log concentration (molar). The Y-axis represents binding, expressed in arbitrary units (AU) fluorescence intensity measured.

FIG. 2A(b) represents the top view of the first row of wells in a 96-well plate (FIG. 2A(a)), showing the fluorescence results obtained for the induced PPAR gamma interaction with a variety of peptides immobilized on each microarray (each well has the same microarray) in the presence of the GW1929 ligand (L), concentrations varying from array to array. FIG. 2A(c) represents examples of the binding curves obtained for peptide motives derived from NCOR1 (SEQ ID NO. 31) and PPRB (SEQ ID NO. 45) respectively. The binding is expressed in arbitrary units (AU) of fluorescence (Y-axis) as a function of ligand concentration [L] (X-axis). FIG. 2B shows the determination of the potency "p", expressed as EC50, and the efficacy "e", expressed as delta binding between the lower and upper plateau of a binding curve (such as shown in FIG. 2A(c)) of the ligand GW1929 for each of the co-regulator derived peptides (SEQ ID NOs 31 and 45).

"Max" indicates the maximum level of binding (100%), "min" the minimal level of binding (ligand-independent binding).

L, Ligand; c, control; M, molar; e, efficacy, p, potency.

Figure 3:
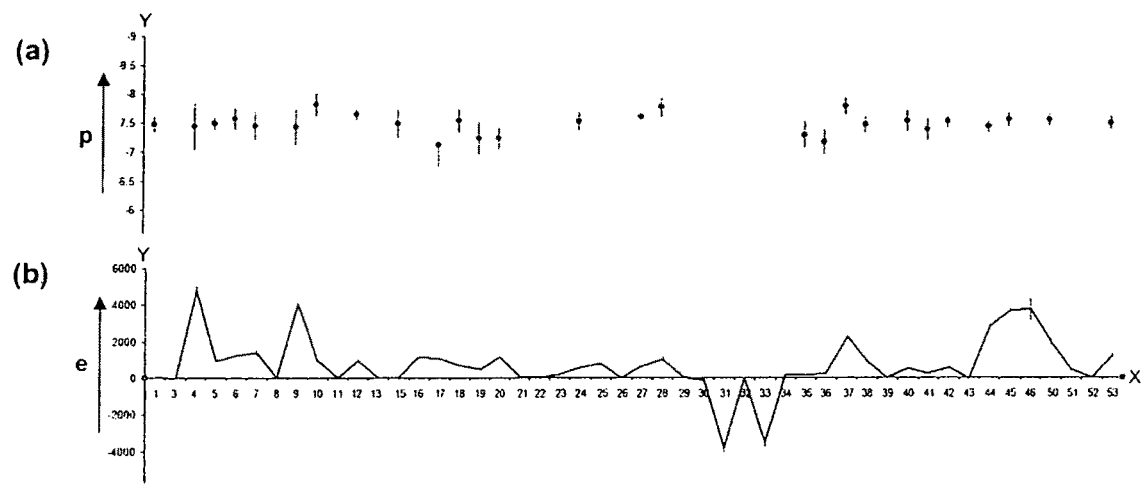

FIG. 3 upper panel (a) shows the potency data expressed as EC50 values (log M), as well as the efficacy data, expressed as delta values between the lower and upper plateau of the binding curves (lower panel (b)) (increase fluorescence intensities) derived for all 48 peptides interrogated in the same assay (SEQ ID NOs 1, 3-13, 15-46, 50-53). The upper Y-axis (upper panel (a)) represents the EC50 values expressed in log molar, the lower Y-axis (lower panel (b)) represents the delta values expressed in arbitrary units. Both upper and lower panels (a) and (b) have the same X-axis representing the above-mentioned 48 different peptides (SEQ ID NOs 1, 3-13, 15-46, and 50-53).

Error bars indicate the Standard Error of the Mean (SEM); p, potency; e, efficacy.

Figure 4:
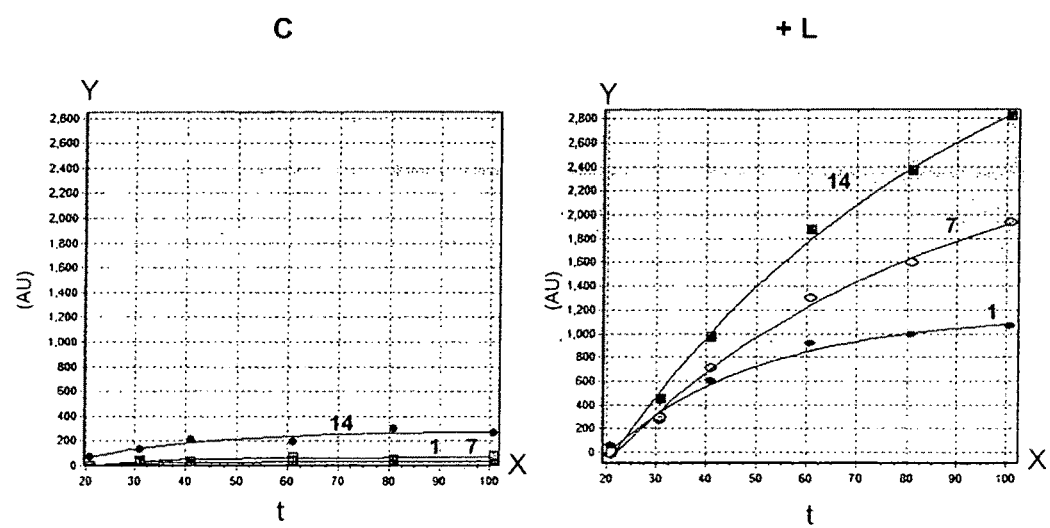

FIG. 4 shows the kinetics of binding of the Glucorticoid Receptor in interactions with a set of 3 of a total of 53 co-regulator derived peptide motifs (SEQ ID NOs 1 to 53), wherein peptide sequences 1, 7 and 14 comprises motifs from the co-regulators CBP, DAX1 and NCOA1 respectively (see Example 3). Time curves of binding in the absence (left-hand panel) and presence (right-hand panel) of the ligand (L) dexamethasone are shown. Binding is expressed as the intensity of fluorescence in arbitrary units (AU) (Y-axis) in function of time (t), plotted on the X-axis and expressed in cycles.

L, ligand; t, time; c, control (absence of ligand).

Figure 5:
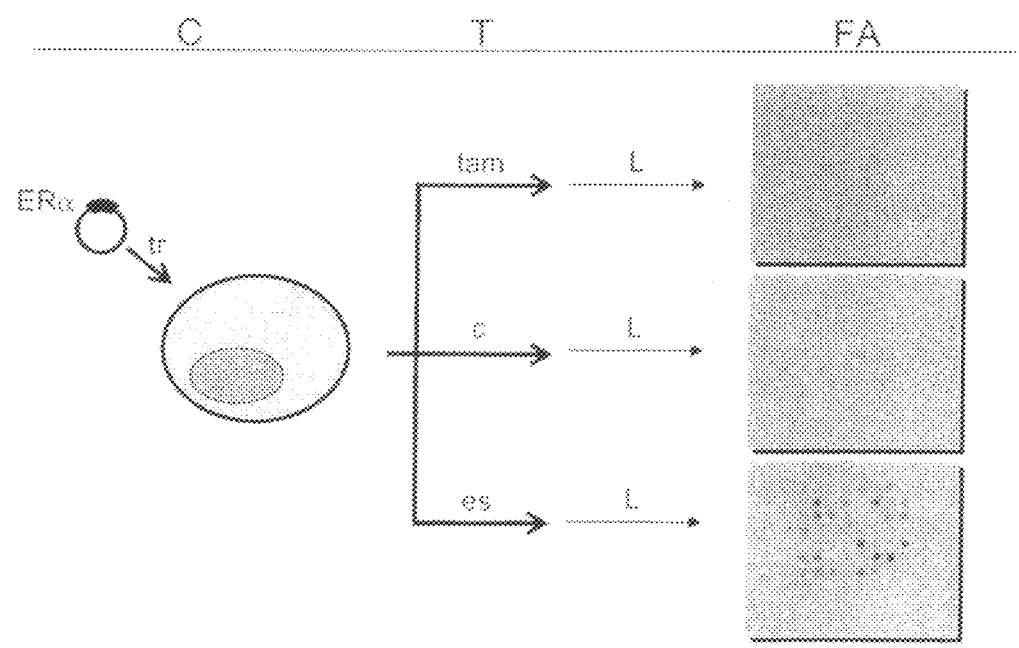

FIG. 5 shows the experimental setup and results of generating ligand (L) induced binding profiles from crude cell extracts (C) as further explained in Example 4. Cells were transfected (tr) with an ER alpha DNA construct (ERα) resulting in expression of the full-length ER alpha, and treated with tamoxifen (tam), estradiol (es) or no ligand (c). Crude extracts were prepared and analysed on microarrays comprising 61 different co-regulator derived peptide motives (SEQ ID NOs 1-61). The fluorescence images in the right panel (microarrays) show the binding profiles as intensity patterns (co-regulator derived motifs). The more intense black a spot, the higher degree of binding of the ER alpha receptor to the peptide motive immobilized on that spot.

C, cells; c, control; ERα, ER alpha construct; es, estradiol; FA, functional analysis; L, lysis (preparation of crude extracts); T, treatment; tam, tamoxifen; tr, transfection.

Figure 6:
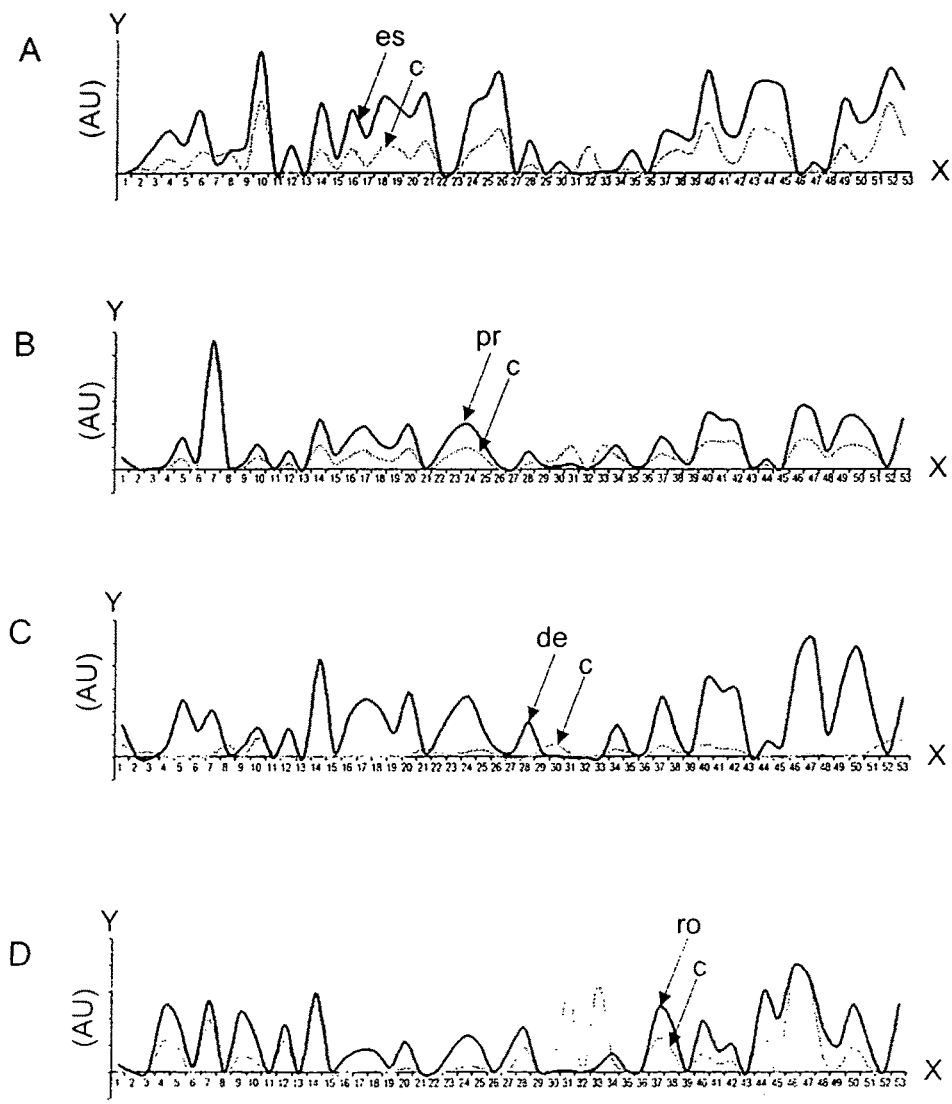
Figure 6:
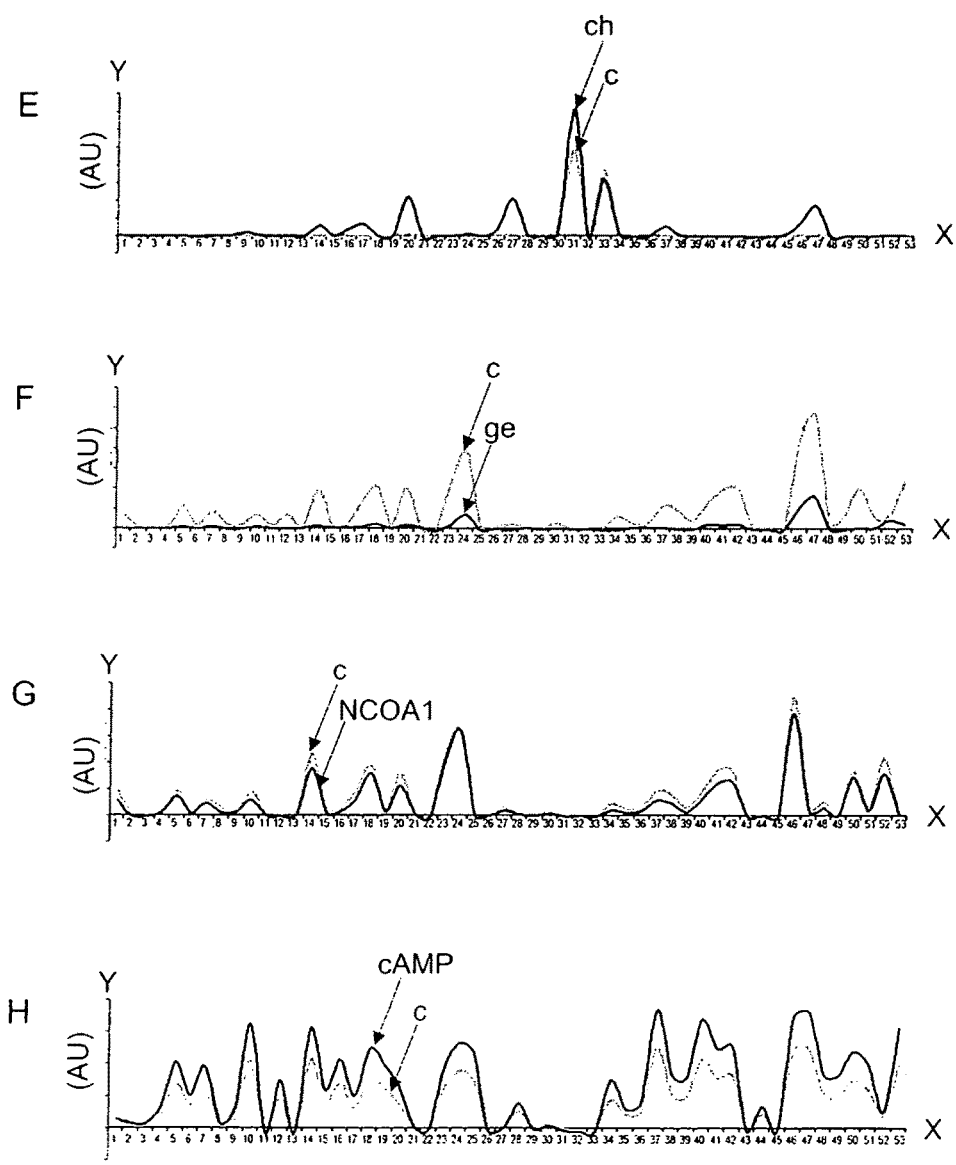

FIG. 6 illustrates the different modulations of multiple different nuclear receptor-co-regulator interactions by multiple different ligands (of various classes) or other agents, as measured in a microarray experiment (see Example 5). The X-axis represents 53 different co-regulator-derived motifs (peptides corresponding to SEQ ID NOs 1-53), and the Y-axis represents the extend of binding detected (fluorescence, arbitrary units (AU)). The binding profile is colored black, and the profile of the control (no modulating agent) is colored gray. FIG. 6A represents the modulation of the Estrogen receptor alpha by the ligand estrogen estradiol; FIG. 6B represents the modulation of the progesteron receptor by progesterone; FIG. 6C represents the modulation of the glucocorticoid receptor by dexamethasone; FIG. 6D represents the modulation of the peroxisome proliferator-activated receptor gamma by rosiglitasone which belongs to the class of the thiazolidenediones; FIG. 6E represents the modulation of the liver x receptor beta by 22[R]hydroxy cholesterol which belongs to the class of hydroxysterols; FIG. 6F represents the modulation of the andogen receptor by dihydroxytestosterone and a gelsolin-derived peptide; FIG. 6G represents the modulation of the androgen receptor by a NCOA1-derived peptoid A (NCOA1) which belongs to the class of peptidomimitics; FIG. 6H represents the modulation of estrogen receptor alpha in control vs. cAMP-stimulated estrogen receptor alpha-transfectants.

es, estradiol; pr, progesterone; de, dexamethasone; ro, rosiglitazone; ch, 22[R]hydroxyl cholesterol; ge, gelsolin-derived peptide; NCOA1, NCOA1 derived peptoid A.

Figure 7:
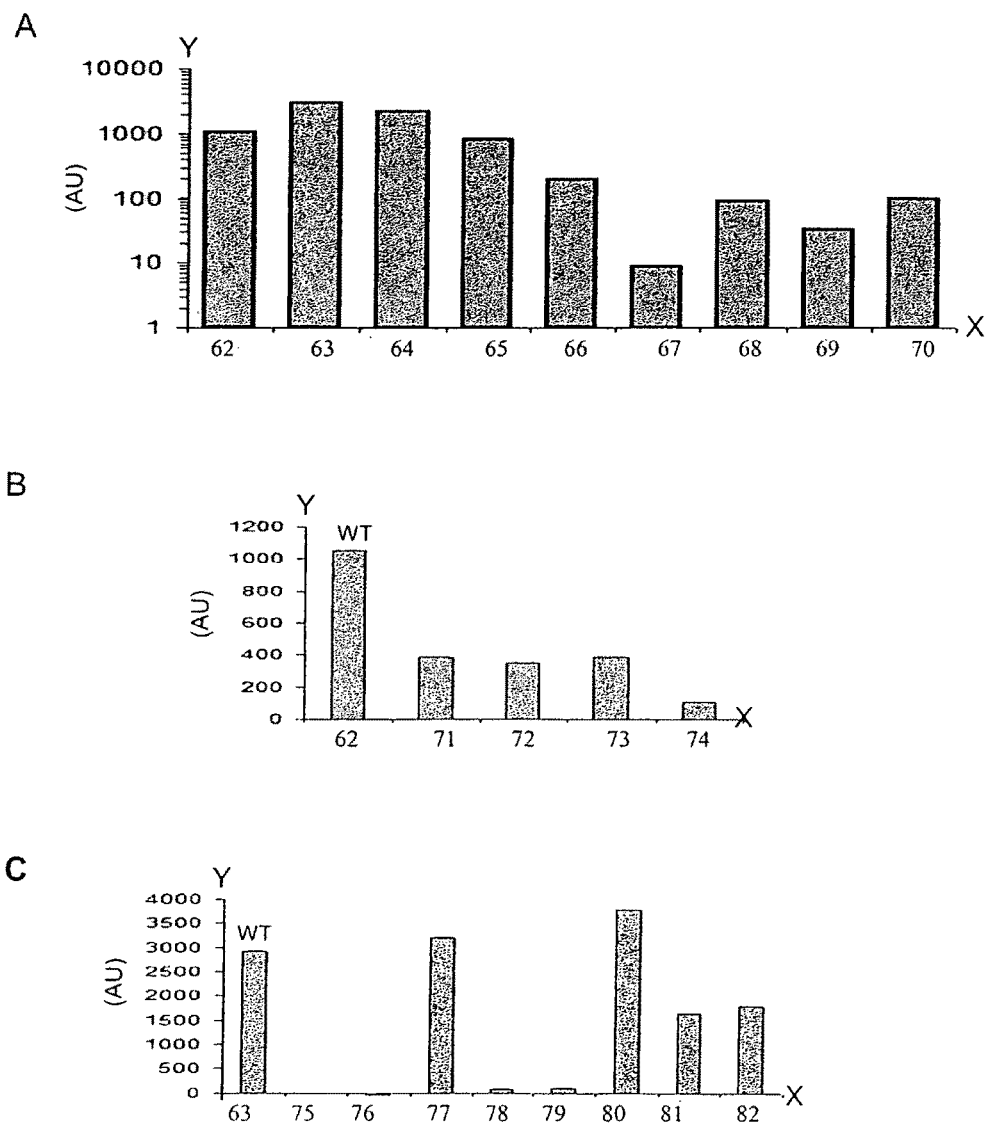

FIG. 7 illustrates the use of co-regulator derived wild-type motifs other than the LxxLL motif and mutated versions thereof, as further explained in Example 6. FIG. 7A shows the results of dihydroxytestosterone (DHT) induced binding of androgen receptor LBD protein to various NR-box motifs including motifs such as FxxFF and FxxLF. The FIGS. 7B and C shows two examples of binding to mutated NR-box motifs derived from the androgen receptor (SEQ ID NO. 62) or derived from the protein gelsolin (SEQ ID NO. 63) respectively. The X-axis shows the SEQ ID NO's of the various peptides that were used; the Y-axis represents the binding expressed as fluorescence intensity in arbitrary units (AU).

WT, wildtype.

Figure 8:
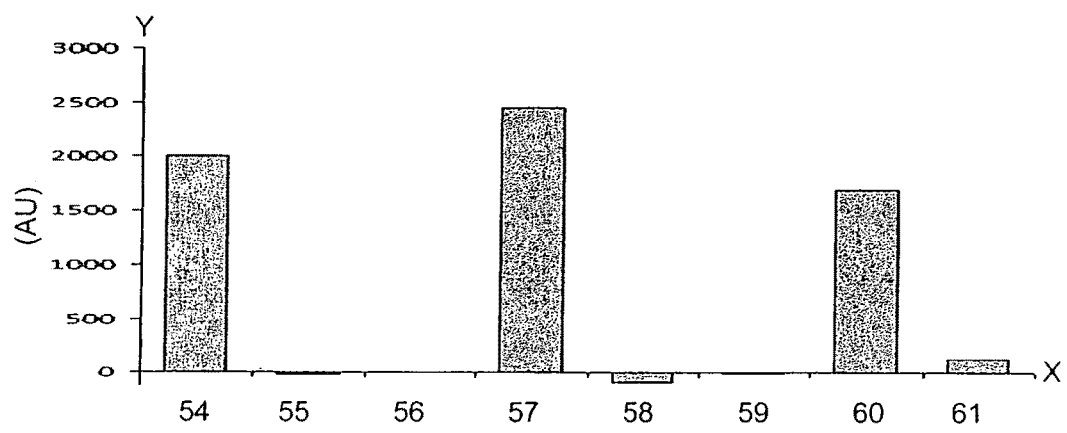

FIG. 8 shows the results obtained after investigating the interaction of E2/cAMP-treated ERalpha transfectants with coregulator (NCOA1, 2 and 3)-derived motifs representing Q-rich domains (Example 6). The X-axis represents the SEQ ID NOs of the Q-rich peptide motifs; the Y-axis represents the binding expressed as fluorescence intensity in arbitrary units (AU).

DETAILED DESCRIPTION OF THE INVENTION

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The present invention relates to modulation of nuclear receptor-co-regulator protein binding by small so-called ligand molecules. Understanding how this binding is affected by ligand interaction with the receptor is believed to be of great value in the design of tissue-specific therapeutics. Typically, nuclear receptor binding to co-activator or co-repressor molecules may be modulated by agonists as well as antagonists which may be receptor-, cell- and/or tissue-specific.

Within the context of the present specification the terms "binding" and "interaction" are used interchangeably and relate to the typical protein-protein binding or interaction as understood by one of skill.

The term "potency" as used within the present specification refers to a compounds capacity to produce an effect on an interaction between NR and a co-regulator. It is typically expressed as an EC50 value. The more potent a compound is the lower concentration is required to show an effect.

The term "efficacy" as used within the present specification refers to the quantity of a compound's effect on an interaction between NR and a co-regulator. It is typically expressed as $\alpha_{Kd}$ value. Alternatively, the efficacy may be expressed as a delta value between absence and the presence of a saturating amount of modulating agent.

To determine the value of a compound for its therapeutic use, the present invention provides a novel multiplex method wherein the compound's potency as well as efficacy is concomitantly determined.

Accordingly, the present invention provides a method for measuring compound efficacy and potency on nuclear receptor-co-regulator interaction, comprising the steps of
(i) co-incubating at least one nuclear receptor and at least one compound under conditions that allow interaction;
(ii) co-incubating the nuclear receptor-compound mixture of step (i) with an array of co-regulators, under conditions that allow compound modulated receptor-co-regulator interaction;
(iii) determination of compound modulated receptor-co-regulator interaction in function of co-regulator concentration, and
(iv) determination of compound modulated receptor-co-regulator interaction in function of compound concentration;
wherein steps (iii) and (iv) are performed in a single assay.

The methods of the present invention allow for the kinetic monitoring of receptor-co-regulator interactions using a variety of different co-regulators or parts thereof, each present in a series of concentrations per co-regulator, in conjunction with a variety of compounds, also each present in a series of concentrations per compound.

Accordingly, within one embodiment of the present invention, a method is provided for measuring compound efficacy and potency on nuclear receptor-co-regulator interaction, wherein said single assay is a kinetic assay.

The term "kinetic" or "kinetic assay" as used within the context of the present invention refers to a determination of compound modulated receptor-co-regulator interaction in function of co-regulator concentration and a determination of compound modulated receptor-co-regulator interaction in function of compound concentration at short intervals or continuously monitored. Advantages of a kinetic assay, compared to an end-point assay, are that the range of measurable activity is high, the reaction monitoring period is short and high enzyme activity can be detected at very short time periods.

A suitable number of compounds that may be screened within the methods according to the present invention ranges between 2 and 50. A very suitable number of compounds that may be screened ranges between 5 and 25. A more suitable number of compounds that may be screened ranges between 7 and 12. A typical number of compounds that may be screened is 8. The number of concentrations per compound usually ranges between 2 and 50. A very suitable number of concentrations per compound usually ranges between 5 and 25. A more suitable number of concentrations per compound usually ranges between 7 and 15. A typical number of concentrations per compound that may be screened is 12.

Typically, the so-called "nuclear receptor ligand-binding domain" members of the nuclear hormone receptor family, also called the classical nuclear receptors, posses the LBD domain which has at least three functions: ligand binding, binding of co-activators or co-repressors, and indirect transcription of RNA. The COOH-terminal portion of the LBD contains an activation function domain or AF helix which is prone to conformational flexibility such that the AF helix may be stabilized into a position that exposes a hydrophobic groove that can accept an amphipathic helix presented by co-regulator proteins. These short helical regions, called NR boxes occurring in multiples within co-regulator proteins, typically contain the LxxLL, or LxxML, or FxxFF, or LxxiL or other motif (where L is leucine, F is phenylalanine, M is Methionine, I is isoleucine, and x is any amino acid).

Thus ligand binding to the LBD triggers a conformational change which expels a bound co-repressor. The site previously occupied by the co-repressor is then free to recruit a co-activator. This ligand-triggered swap of a co-repressor for a co-activator is the mechanism by which ligand binding leads to the transcriptional activation of target genes. The classical LBD, characterized by an AF helix recognizing the NR box comprising the LxxLL, or LxxML, or FxxFF, or LxxIL or other motif of co-regulators, is the binding site for all nuclear receptor targeted drugs to date. Since LBDs are attractive drug targets, much effort by many research groups is now in progress to identify novel LBDs that may have particular helixes which may expose a novel site to bind with co-regulators through motifs other than e.g. LxxLL.

The present invention accordingly contemplates the use of any co-regulator residues or amino acid sequences that modulate its interaction with a nuclear receptor.

Within the methods of the present invention, co-regulators may be represented by protein sequences. However increased analysis efficiency may be obtained when co-regulators are represented by peptide surrogates.

Accordingly, within one embodiment of the present invention, a method is provided for measuring compound efficacy and potency on nuclear receptor-co-regulator interaction, wherein the co-regulators are proteins or peptides.

The peptides usually have a length ranging between 6 and 35 amino acids. A very suitable peptide length ranges between 10 and 30 amino acids. A typical peptide length is 25 amino acids. Each peptide arrayed within the array of co-regulators has a unique sequence.

Co-regulators may be either co-activators or co-repressors. Recently, a number of co-regulatory proteins for nuclear receptors have been identified, and have been shown to act either as co-activators or as co-repressors (reviewed in Horwitz et al., 1996; Shibata et al., 1997; Glass et al., 1997). Among the members of a growing family of co-activators are CBP and members of the SRC-1 gene family including SRC-1/p160 (Onate et al., 1995, *Science* 270:1354-1357; Halachmi et al., 1994, *Science* 264:1455-1458; Kamei et al., 1996, *Cell* 85:403-414), TIF2/GRIP-1 (Voegel et al., 1996, *The EMBO Journal* 15(14):3667-3675; Hong et al., 1996, *Proc. Natl. Acad. Sci. USA* 93:4948-4952; Ding et al., 1998, *Molecular Endocrinology* 12:302-313), and CBP/p300 (Chakravarti et al., 1996, *Nature* 383:99-103; Hanstein et al., 1996, *Proc. Natl. Acad. Sci. USA* 93:11540-11545) which function as co-activators of nuclear receptors, and also RIP140 (Cavailles et al., 1994, *Proc. Natl. Acad. Sci. USA* 91:10009-10013; Cavailles et al., 1995, *The EMBO Journal* 14(15):3741-3751), TIF1 (Le Douarin et al., 1995 *The EMBO Journal* 14(9):2020-2033) and TRIP1/SUG-1 (Lee et al., 1995, Nature 374:91-94; vom Baur et al., 1996, *The EMBO Journal* 15(1):110-124), the functions of which are not clearly defined. Most of these co-regulators of nuclear receptors have a molecular weight around 160 kDa.

Accordingly, in one embodiment of the present invention, a method is provided for measuring compound efficacy and potency on nuclear receptor-co-regulator interaction, wherein said co-regulators are co-activators and/or co-repressors, including fragments thereof, containing a binding domain for the nuclear receptor.

Said binding domain usually comprises a typical residue or an amino acid core consensus. Typical examples of amino acid core consensus sequences are LxxLL, LxxML, FxxFF, and LxxIL (L, leucine; F phenylalanine; M, Methionine; I, isoleucine and x, any amino acid) which is known to be necessary and sufficient to mediate the binding of co-regulator proteins to liganded classical nuclear receptors. In addition, co-regulator motifs other than the above mentioned which may enable interaction with an LBD are equally contemplated within the present invention.

Accordingly, in one embodiment of the present invention, a method is provided for measuring compound efficacy and potency on nuclear receptor-co-regulator interaction, wherein said co-regulators are in the form of peptides comprising the amino acid core consensus sequence chosen from the group comprising LxxLL, LxxML, FxxFF, and LxxIL.

Within the methods of the present invention, the peptide array format may be chosen out of various formats including, but not limited to free peptides in separate vials such as small eppendorf vials with each unique peptide sequence per vial, peptides coupled onto microspheres with each unique peptide sequence onto a separate microsphere, or peptides immobilized onto a solid support in the format of a microarray having each unique peptide sequence coupled onto a distinct spot on the solid surface. Typically within the methods of the present invention, the peptide array format is a microarray.

Accordingly, within one embodiment of the present invention, a method is provided for measuring compound efficacy and potency on nuclear receptor-co-regulator interaction, wherein said array of co-regulators is a microarray of co-regulators.

The expression "immobilized" or "coupled" onto a microsphere, solid support or other carrier as used in the present specification refers to the attachment or adherence of one or more molecules to the surface of the carrier including attachment or adherence to the inner surface of said carrier in the case of e.g. a porous or flow-through solid support.

A number of materials suitable for use as a microarray solid support in the present invention have been described in the art. Materials particularly suitable for use as microarray solid support in the present invention include any type of solid support, including solid supports, known in the art, e.g. glass microscope slides, silicon chips or nylon membranes.

Particular suitable microarray solid supports for use within the methods of the present invention are porous supports. The term "porous support" as used in the present specification refers to a support possessing or full of pores, wherein the term "pore" refers to a minute opening or microchannel by which matter may be either absorbed or passed through. Particularly, where the pores allow passing-through of matter, the support is likely to be permeable.

Particular useful porous supports for employment within the methods described in the present specification are 3-dimensional supports, which allow pressurized movement of fluid up and down (i.e., cycling) through the pores, e.g. the sample solution, through its structure.

As such, particular useful porous supports for use within the present methods possess a flow-through nature. The channels or pores through a flow-through solid support may be discrete or branched having extremities typically ending at the corresponding top and bottom surface of the solid support. In contrast with two-dimensional supports, 3-dimensional microarray supports suitable within the methods as described herein give significantly reduced hybridization times and increased signal and signal-to-noise ratios.

Accordingly, in one embodiment of the present invention, a method is provided for measuring compound efficacy and potency on nuclear receptor-co-regulator interaction, wherein said microarray is a flow-through microarray.

Suitable 3-dimensional solid supports for use within the present invention may be manufactured out of, for example, a metal, a ceramic metal oxide or an organic polymer. In view of strength and rigidity, a metal or a ceramic metal oxide may be used. Above all, in view of heat resistance and chemicals resistance, a metal oxide may be used. In addition, metal oxides provide a support having both a high channel density and a high porosity, allowing high density arrays comprising different first binding substances per unit of the surface for sample application. In addition, metal oxides are highly transparent for visible light. Metal oxides are relatively cheap that do not require the use of any typical microfabrication technology and, that offers an improved control over the liquid distribution over the surface of the support, such as an electrochemically manufactured metal oxide membrane.

Typically, flow-through microarray solid supports such as metal oxide solid supports may undergo positive and negative pressures. By applying alternative positive and negative pressure to the arrays a sample solution may be dynamically pumped up and down through the support pores. Said dynamical pumping allows immediate real-time detection of generated products from a reaction which takes place within the pores of the support. The expression "positive pressure" relates to a pressure higher than the standard atmospheric pressure of 1 atm. The expression "negative pressure" relates to a pressure lower than the standard atmospheric pressure of 1 atm. A negative pressure is also referred to as vacuum pressure.

Metal oxide supports or membranes suitable for use within the methods of the present invention may be anodic oxide films. WO 99/02266 which discloses the Anopore™ porous membrane or support is exemplary in this respect, and is specifically incorporated by reference in the present invention.

As well known in the art, aluminum metal may be anodized in an electrolyte to produce an anodic oxide film. The anodization process results in a system of larger pores extending from one face, e.g., the top surface of a solid support, and interconnects with a system of smaller pores extending from the other face or bottom surface. Pore size is determined by the minimum diameters of the smaller pores, while flow rates are determined largely by the length of the smaller pores, which can be made very short. Accordingly, such membranes may have oriented through-going partially branched channels with well-controlled diameter and useful chemical surface properties. The expression "partially branched" as used within the present description refers to larger channels as being branched at one end into a series of smaller channels. The larger channels which predominantly run in parallel are usually mutually interconnected, resulting in so-called substantially discrete channels, and a similar interconnection may appear between the smaller channels.

Useful thickness of solid supports or membranes suitable for use within the methods of the present invention may for instance range from 30 µm to 150 µm (including thicknesses of 30 40, 50, 60, 70, 80, 90, 100, 110, 120, 130, 140 and 150 µm). A particular suitable example of support thickness is 60 µm.

A suitable support pore diameter for porous solid supports, in particular flow-through solid supports, ranges from 150 to 250 nm including 150, 160, 170, 180, 190, 200, 210, 220, 230, 240 and 250 nm. A particular suitable example of pore diameter is 200 nm.

Within the methods of the present invention, co-regulators are arrayed, typically in a microarray format comprising various spots with each spot having immobilized thereto a unique peptide sequence representing the typical LxxLL, LxxML, FxxFF, LxxIL or other binding region of a co-activator or a co-repressor. Typically, a microarray comprises tens to hundreds spots or small spatial areas on the solid surface. Within the methods of the present invention the number of spots on a microarray ranges between 50 and 1000 spots. A very suitable number of spots ranges between 150 and 700 spots. A typical number of spots on a microarray for use within the methods of the present invention is 400, corresponding to a spot density of about 25 spots per mm$^2$.

The number of spots on a microarray suitable for use within the present methods may accommodate the immobilization of various different peptides as well as various different peptide concentrations. The latter allows the determination of a compound's efficacy.

Accordingly, in one embodiment of the present invention a method is provided for measuring compound efficacy and potency on nuclear receptor-co-regulator interaction, wherein said microarray of co-regulators comprises various co-regulators with various concentrations per co-regulator.

The number of different peptide sequences in an array of co-regulator's within the methods of the present invention typically ranges between 2 and 48 unique peptide sequences. In a microarray format, this would be represented in 2 to 48 spots on the solid support. The series of peptide concentrations for a single peptide usually ranges between 2 to 80 different concentrations per unique peptide sequence. A very suitable series of concentrations for a peptide ranges between 3 to 60, 3 to 40 and 3 to 20. A typical number of different concentration samples of a peptide sequence for use within the methods of the present invention is between 2 and 10. Thus for each unique peptide sequence in an array of co-regulators, typically between 2 and 10 different concentrations thereof may be enclosed within the assay. A peptide concentration series for making arrays for a particular unique peptide sequence that may be immobilized on a microarray suitable for use within the present invention may start at 1 mM to with between 2 and 10 dilutions in steps of 1.5-10 fold dilutions, or starting from a higher initial concentration up to 100 mM.

Besides a kinetic determination of nuclear receptor-co-regulator binding in function of co-regulator concentration, the methods of the present invention equally and concomitantly allow the kinetic determination of nuclear receptor-co-regulator binding in function of compound concentration. Thereto, an array of peptide arrays is set up, wherein each peptide array is co-incubated with a compound-receptor sample, wherein each said sample comprises a different compound and/or a different compound concentration. As such the compound's potency, besides is efficacy, can be measured in a single assay. The term assay as used in the present specification refers to a single experiment wherein a compound's potency and efficacy are determined concomitantly and wherein on or more peptide arrays, e.g., peptide microarrays, may be employed.

An array of peptide arrays may be accomplished by using for example a 96-well plate having one peptide array fixed as a bottom per well. Within the methods of the present invention, usually the wells are provided with peptide array duplicates, i.e. each well bottom is made out of the same peptide array. In such a multi-well set-up, co-incubation of a nuclear receptor with a number of different compounds may be done within at least a same number of corresponding wells; e.g., an assay involving 10 compounds requires at least 10 wells. Alternatively, different peptide arrays may occupy different wells. For example, the variety of co-regulator concentrations may be present by changing the concentration of one or more co-regulators per well. The said co-incubation may be directly on the microarray. Alternatively, co-incubation of receptor and compound may be performed outside the said wells and brought into the wells after lapsing of the co-incubation time. This co-incubation time may range from 1 minute up to 24 hours.

Accordingly, in one embodiment of the present invention a method is provided for measuring compound efficacy and potency on nuclear receptor-co-regulator interaction, wherein duplicates of said microarray are imbedded in a multi-well plate.

Once the co-incubation time for receptor and compound has lapsed and the mixture has been brought onto a peptide microarray, a further co-incubation between the nuclear receptor-compound mixture and the peptides may be performed. In case of a porous flow-through solid support, the mixture may be co-incubated through dynamic up and down pumping of the mixture through the pores of the support.

Within the multiplex methods of the present invention, a number of parameters may be varied from peptide array to peptide array. With respect to the length of the NR, the LBD may be present, or additional domains may be present, or mutations in the LBD (if present) or additional domains may be present, which may be of importance in the regulation of the protein function may be included. Also, mixtures of NRs may be applied; the NR may work as a hetero-dimer which may affect their function. Further, the source of a same NR may be varied over various peptide arrays, i.e., NRs may originate from wildtype or mutant recombinant proteins (for instance the LBD), wildtype proteins, mutant proteins, full-length proteins, crude-extracts/lysates of NR transfectants, or samples (cell lines, tissues, etc.) comprising endogenous NR. Further, from well to well in a multi-well plate, different compounds, separate or combined may be applied or present in a pre-co-incubation mix with a receptor and in addition, compound concentrations may be varied.

Compounds useful within the methods of the present invention may include natural or synthetic hormones, pheromones, neurotransmitters, peptides, biogenic amines, amino acids, ions, lipids, nucleotides, enzymes, vitamins and small molecules, among others. These may have a known activity but may also be compounds without an identified activity. Non-limiting examples of drugs or agents having already a certain activity or activity profile include enzymes that induce NR post-translational modifications (PTM) such as kinases, phosphatases, ubiquitinases, sumoylases, etc.; hormones such as e.g., androgens such as steroids, including the sex hormones responsible for controlling sexual and reproductive development, corticosteroids such as glucocorticoids which regulate responses to stress and mineral corticoids, retinoids, thyroid hormone; prostanoids such as prostaglandins, thromboxanes and prostacyclins, progesterone, framesoids; and vitamins A and D (e.g., vitamin D3) and derivatives thereof. In particular, in respect of the estrogen receptor a (ERα), several classic, well-known characterized ligands are for example estrogens such as estrone (E1), estradiol (E2) and estriol (E3), DES, raloxifene, 4-OH tamoxifen, idoxifene, levormeloxifene and GW7604.

Accordingly, within one embodiment of the present invention, a method is provided for measuring compound efficacy and potency on nuclear receptor-co-regulator interaction, wherein said compound is selected from the group comprising peptides, peptoids, biogenic amines, amino acids, ions, lipids, nucleotides, enzymes, vitamins and hormones.

Accordingly, within one embodiment of the present invention, a method is provided for measuring compound efficacy and potency on nuclear receptor-co-regulator interaction, wherein said compound is selected from the group comprising enzymes, androgens, corticosteroids, estrogens, prostanoids, farnesoids, progesterone, vitamins A and D, thyroid hormone, retinoic acid, fatty acids, prostaglandin, cholesterol, oxysterols, bile acids, pProgesterone and testosterone.

In accordance, the nuclear receptor family comprises receptors for glucocorticoids (GRs), androgens (ARs), mineral corticoids (MRs), progestins (PRs), estrogens (ERs), thyroid hormones (TRs), vitamin D (VDRs), retinoids (RARs and RXRs), steroids, peroxisomes (XPARs and PPARs), oxysterols (LXRs), bile acids (FXRs), and icosanoids (IRs).

The so-called "orphan receptors" for which ligands have not been identified are also part of the nuclear receptor super family, as they are structurally homologous to the classic nuclear receptors, such as steroid and thyroid receptors.

Accordingly, in one embodiment of the present invention, a method is provided for measuring compound efficacy and potency on nuclear receptor-co-regulator interaction, wherein said nuclear receptor is selected from the group comprising receptors for glucocorticoids (GRs), androgens (ARs), mineral corticoids (MRs), progestins (PRs), estrogens (ERs), thyroid hormones (TRs), vitamin D (VDRs), retinoids (RARs and RXRs), steroids, peroxisomes (XPARs and PPARs) and icosanoids (IRs), oxysterols (LXRs), bile acids (FXRs), and orphan receptors.

Within the multiplex methods of the present invention, a number of parameters may be varied within a same peptide array. With respect to the co-regulator sequences, any sequence may be used. Usually, co-regulator sequences as used within the present invention comprise known characteristic motifs such as the NR box LxxLL, LxxML, FxxFF, LxxIL or other motif. Within a same peptide array, the length of peptide sequences may be varied as well as the number of amino acids flanking the NR box. Wild type sequences may be mutated. Further, also the concentration of the immobilized peptides may be varied from spot to spot within a peptide array. This is in particular useful for Kd determination.

The present invention relates to the analysis of NR-compound samples to identify and quantify interactions with an array of co-regulators. Typically a reporter system is included which provides a detectable signal indicative of the formation of compound modulated NR-co-regulator interactions.

The present invention provides for the monitoring of effect(s) of a ligand or modulator molecule on activity and specificity of a co-regulator for a nuclear receptor.

The detection signal can be in the form of a fluorescent signal, chemiluminescent signal, or a calorimetric signal. A particular useful detector system in the methods as described herein includes labeling of the NR (LBD) to provide a detection system which may generate a detectable signal which is indicative of the interaction of an analyte with an immobilized target. The detectable label may be a direct detectable label for instance a fluorescent label on the NR or may be an indirect label using an for instance an antibody against an epitope on the NR which does not influence the binding reaction between the NR and the NR box. This antibody may be labeled directly with for instance a fluorescent label or indirectly using a secondary antibody with a detectable label for instance a fluorescent label.

The term "label" as used in this specification refers to a molecule propagating a signal to aid in detection and quantification. Said signal may be detected either visually (e.g., because it has color, or generates a color product, or emits fluorescence) or by use of a detector that detects properties of the reporter molecule (e.g., radioactivity, magnetic field, etc.). In the present specification, labels allow for the detection of the interaction between NR and co-regulator sequence. Detectable labels suitable for use in the present invention include but are not limited to any composition detectable by spectroscopic, photochemical, biochemical, immunochemical, electrical, optical or chemical means. Where appropriate, the system may contain more labels producing different signals which may be a component of, or released by, an interaction event. Any combination of labels, e.g. first and second labels, first, second, and third labels, etc. may be employed for analyte sets, provided the labels are distinguishable from one another. Examples of distinguishable labels are well-known in the art and include: two or more different wavelength fluorescent dyes, such as Cy3 and Cy5 or Alexa 488, Alexa 542 and Bodipy 630/650; two or more isotopes with different energy of emission, such as $^{32}$P and $^{33}$P; labels which generate signals under different treatment conditions, like temperature, pH treatment by additional chemical agents, etc.; and labels which generate signals at different time points after treatment.

Particular suitable labels that may be employed in the present invention may be chromogens including those that absorb light in a distinctive range of wavelengths so that a colour may be observed or, alternatively, that emit light when irradiated with radiation of a particular wavelength or wavelength range, e.g., fluorescent molecules. Particular useful fluorescent labels include, by way of example and not limitation, fluorescein isothiocyanate (FITC), rhodamine, malachite green, Oregon green, Texas Red, Congo red, SybrGreen, phycoerythrin, allophycocyanin, 6-carboxyfluorescein (6-FAM), 2',7'-dimethoxy-4',5'-dichloro-6-carboxyfluorescein (JOE), 6-carboxy X-rhodamine (ROX), 6-carboxy-2',4', 7',4,7-hexachlorofluorescein (HEX), 5-carboxyfluorescein (5-FAM), N,N,N',N'-tetramethyl-6-carboxyrhodamine (TAMRA), cyanine dyes (e.g. Cy5, Cy3), BODIPY dyes (e.g. BODIPY 630/650, Alexa 488, Alexa542, etc), green fluorescent protein (GFP), blue fluorescent protein (BFP), yellow fluorescent protein (YFP), red fluorescent protein (RFP), and the like, (see, e.g., Molecular Probes, Eugene, Oreg., USA).

The detection of a signal profile allows determination of the specificity of an NR-co-regulator interaction modulated by a compound. The modulation of the interaction activity and/or specificity may be deduced from a comparison of the signal profile with a signal profile drawn up in the presence of increasing or decreasing co-regulator concentrations, including the absence of co-regulator.

The methods of the present invention thus allow the determination of a compound's potency by varying its concentration from peptide array to peptide array (i.e., between peptide arrays), while concomitantly the NR-co-regulator Kd may be determined by varying the concentration of the immobilized co-regulator sequences within a same peptide array. Further concomitantly, efficacy may be determined by comparing the Kd obtained within a single peptide array in the absence of a compound with the Kd obtained within another single peptide array in the presence of a compound.

It will be well appreciated that the methods as described herein may also be employed to study compound modulated binding events other than NR binding events. As such the methods as described herein may be employed for measuring compound efficacy and potency on e.g., interactions involving other receptors such as the G-coupled receptor (GPCR), 7-transmembrane receptor (7™), and ion channels. In addition, enzyme-substrate interactions, e.g. kinase assays may be monitored using the methods of the present invention.

Accordingly, it is a further object of the present invention to provide methods as described herein wherein a compound's efficacy and potency is measured on co-regulator interactions with a protein other the a nuclear receptor chosen from the group comprising G-coupled receptor (GPCR), 7-transmembrane receptor (7TM), ion channel and enzymes.

The methods according to the present invention are useful in a number of applications.

In one embodiment, the present invention provides for the use of methods as described herein for compound profiling.

In another embodiment, the present invention provides for the use of methods as described herein for the concomitant determination of compound potency and efficacy. This means that the methods according to the present invention allow the determination of compound potency and efficacy in a same or single experimental setting.

The following examples are offered by way of illustration, and not by way of limitation.

EXAMPLES

The peptide sequences used in the various experimental set-ups as further explained in Examples 1 to 6 are represented in Table 1. The peptide name in column 2 (referring to the Swissprot name in column 4, human, unless otherwise indicated) includes a reference to the motif and position of the motif in the full protein sequence (source: column 5) followed by the positions of the first and last amino acid of the motif-flanking amino acids and (optional) the mutation of the wild type.

TABLE 1

| SEQ ID NO. | Peptide sequence | Name of peptide | SwissProt (name) | Swiss Prot AccNr |
|---|---|---|---|---|
| 1 | SVQPPRSISPSALQDLLRRKSP | CBP_LxxLL2067_2055_2077 | CBP_HUMAN | Q92793 |
| 2 | TADPEKRKLIQQQLVLLLHAHKCQ | CBP_LxxLL358_345_368 | CBP_HUMAN | Q92793 |
| 3 | TADPEKRKLIQQQLVLLLHAHKSQ | CBP_LXxLL358_345_368_C367S | CBP_HUMAN | Q92793 |
| 4 | GNLVPDAASKHKQLSELLRGGSGS | CBP_LxxLL70_57_80 | CBP_HUMAN | Q92793 |
| 5 | GEDHPRQGSILYSLLTSSKQTHVA | DAX1_LxxLL146_136_159 | DAX1_HUMAN | P51843 |
| 6 | MAGENH0WQGSILYNMLMSAKQT | DAX1_LxxML13_1_23 | DAX1_HUMAN | P51843 |
| 7 | FSGKDHPRQGSILYSMLTSAKQT | DAX1_LxxML80_68_90_C69S | DAX1_HUMAN | P51843 |
| 8 | SPLKPGTVSQQALQNLLRTLRSP | EP300_LxxLL2051_2039_2061 | EP300_HUMAN | Q09472 |
| 9 | GMVQDAASKHKQLSELLRSGSSP | EP300_LXxLL81_69_91 | EP300_HUMAN | Q09472 |
| 10 | PLGSAMLRPNPILARLLRAHGAP | IKBB_LxxLL289_277_299 | IKBB_HUMAN | Q15653 |
| 11 | LHLAVIHOHEPFLDFLLGFSAGT | IKBB_LxxLL74_62_84 | IKBB_HUMAN | Q15653 |
| 12 | PLVSQNNEQGSTLRDLLTTTAGK | JMJ1C_LxxLL37_25_47 | JMJ1C_HUMAN | Q15652 |
| 13 | QWVSSLNEREQELHNLLEVVSQS | KIF11_LxxLL845_833_855_C855S | KiF11_HUMAN | P52732 |

TABLE 1-continued

| SEQ ID NO. | Peptide sequence | Name of peptide | SwissProt (name) | Swiss Prot AccNr |
|---|---|---|---|---|
| 14 | TSGPQTPQAQQKSLLQQLLTE | NCOA1_LxxLL1435_1421_1441 | NCOA1_HUMAN | Q15788 |
| 15 | SDGDSKYSQTSHKLVQLLTTTAEQ | NCOA1_LxxLL633_620_643 | NCOA1_HUMAN | Q15788 |
| 16 | PSSHSSLTERHKILHRLLQEGSPS | NCOA1_LxxLL690_677_700 | NCOA1_HUMAN | Q15788 |
| 17 | ASKKKESKDHQLLRYLLDKDEKD | NCQA1_LxxLL749_737_759 | NCOA1_HUMAN | Q15788 |
| 18 | GQSRLHDSKGQTKLLQLLTTKSDQ | NCOA2_LxxLL641_628_651 | NCOA2_HUMAN | Q15596 |
| 19 | STHGTSLKEKHKILHRLLQDSSSP | NCOA2_LxxLL690_677_700 | NCOA2_HUMAN | Q15596 |
| 20 | EPVSPKKKENALLRYLLDKDDTK | NCOA2_LxxLL745_733_755 | NCOA2_HUMAN | Q15596 |
| 21 | SQSTFNNPRPGQLGRLLPNQNLP | NCOA2_LxxLL878_866_888 | NCOA2_HUMAN | Q15596 |
| 22 | KKKGQGVIDKDSLGPLLLQALDG | NCOA3_LxxLL113_102_123_N-KKK | NCOA3_HUMAN | Q9Y609 |
| 23 | QRGPLESKGHKKLLQLLTCSSDD | NCOA3_LxxLL621_609_631 | NCOA3_HUMAN | Q9Y6Q9 |
| 24 | QRGPLESKGHKKLLQLLTSSSDD | NCOA3_LxxLL621_609_631_C627S | NCOA3_HUMAN | Q9Y609 |
| 25 | MHGSLLQEKHRILHKLLQNGNSP | NCOA3_LxxLL685_673_695 | NCOA3_HUMAN | Q9Y609 |
| 26 | HGSQNRPLLRNSLDDLLGPPSNA | NCOA3_MOUSE_LxxLL1041_1029_1051 | NC0A3_MOUSE | Q09000 |
| 27 | LVSPAMREAPTSLSQLLDNSGAP | NCOA6_LxXLL1491_1479_1501 | NCOA6_HUMAN | Q14686 |
| 28 | PVNKDVTLTSPLLVNLLQSDISA | NCOA6_LxxLL887_875_897 | NCOA6_HUMAN | Q14886 |
| 29 | MGQVPRTHRLITLADHICQIITQ | NCOR1_LxxHI2051_2039_2061 | NOOR1_HUMAN | O75376 |
| 30 | MGQVPRTHRLITLADHISQIITQ | NCOR1_LxxHI2051_2039_2061_C2056S | NC0R1_HUMAN | O75376 |
| 31 | GHSFADPASNLGLEDIIRKALMG | NOOR1_LxxII2263_2251_2273 | NCOR1_HUMAN | O75376 |
| 32 | APGVKGHQRVVTLAQHISEVITQ | NCOR2_LxxHI2135_2123_2145 | NCOR2_HUMAN | Q9Y618 |
| 33 | QAVQEHASTNMGLEAIIRKALMG | NCOR2_LxxII2342_2330_2352 | NCOR2_HUMAN | Q9Y618 |
| 34 | DSVRKGKQDSTLLASLLQSFSSR | NRIP1_LxxLL133_121_143 | NRIP1_HUMAN | P48552 |
| 35 | KDLRCYGVASSHLKTLLKKSKVK | NRIP1_LxxLL185_173_195 | NRIP1_HUMAN | P48552 |
| 36 | KDLRSYGVASSHLKTLLKKSKVK | NRIP1_LxxLL185_173_195_C177S | NRIP1_HUMAN | P46552 |
| 37 | RNNIKQAANNSLLLHLLKSQTIP | NRIP1_LxxLL380_368_390 | NRIP1 HUMAN | P46552 |
| 38 | KNSKLNSHQIVTLLQLLLGHKNE | NRIP1_LxxLL500_488_510 | NRIP1_HUMAN | P48552 |
| 39 | SEIENLLERRTVLQLLLGNPTKG | NRIP1_LxxLL713_701_723 | NRIP1 HUMAN | P48552 |
| 40 | PVSPQDFSFSKNGLLSRLLRQNODSYL | NRIP1_LxxLL819_805_831 | NRIP1_HUMAN | P48552 |
| 41 | RSWARESKSFNVLKQLLLSENCV | NRIP1_LxxLL936_924_946 | NRIP1_HUMAN | P48552 |
| 42 | RSWARESKSFNVLKQLLLSENSV | NRIP1_LxxLL936_924_946_C945S | NRIP1 _HUMAN | P48552 |
| 43 | EEDADTKQVYFYLFKLLRKSILQ | PCAF_LxxLL190_178_200 | PCAF_HUMAN | Q92831 |
| 44 | HGEDFSKVSQNPILTSLLQITGNG | PPRB_LxxLL604_591_614 | PPRB_HUMAN | Q15648 |
| 45 | VSSMAGNTKNHPMLMNLLKDNPAQ | PPRB_LxxLL645_632_655 | PPRB HUMAN | Q15648 |
| 46 | DGTPPPQEAEEPSLLKKLLLAPANTQ | PRGC1_LxxLL144_130_155 | PRGC1_HUMAN | Q9U8K2 |
| 47 | PPQEAEEPSLLKKLLLAPANT | PRGC1_LxxLL144_134_154 | PRGC1_HUMAN | Q9UBK2 |
| 48 | PAPEVDELSLLQKLLLATSYP | PRGC2_LxxLL156_146_166 | PRGC2_HUMAN | Q86YN6 |
| 49 | AEFSILRELLAQDVLCDVSKP | PRGC2_LxxLL343_338_358 | PRGC2_HUMAN | Q86YN6 |
| 50 | TFEVAEAPVPSILKKILLEEPSS | SHP_LxxIL118_106_128 | SHP_HUMAN | Q15466 |
| 51 | SPSQGAASRPAILYALLSSSLKA | SHP_LxxLL21_9_31_C9S_C11S | SHP_HUMAN | Q15466 |

TABLE 1-continued

| SEQ ID NO. | Peptide sequence | Name of peptide | SwissProt (name) | Swiss Prot AccNr |
|---|---|---|---|---|
| 52 | FVNLYTRERQDRLAVLLPGRHPS | TRIP4_LxxLL161_149_171_C171s | TRIP4_HUMAN | Q15650 |
| 53 | LQNLKNLGESATLRSLLLNPHLR | ZNHl3_LxxLL101_89_111 | ZNHL3_HUMAN | Q15649 |
| 54 | QLRLQLQQRLQGQQ | NCOA1_Q1053_1053_1066 | NCOA1_HUMAN | Q15788 |
| 55 | QPPLNAQMLAQRQR | NCOA1_Q1105_1101_1114 | NCOA1_HUMAN | Q15788 |
| 56 | PQGAPQQFPYPPNY | NCOA1_Q1164_1160_1173 | NCOA1_HUMAN | Q15788 |
| 57 | QLRLQLQHRLQAQQ | NCOA2_Q1188_1188_1201 | NCOA2_HUMAN | Q15596 |
| 58 | QAPINAQMLAQRQR | NCOA2_Q1232_1227_1240 | NCOA2_HUMAN | Q15596 |
| 59 | PQANAQQFPFPPNY | NCOA2_Q1296_1292_1305 | NCOA2_HUMAN | Q15596 |
| 60 | QLRMQLQQRLQGQQ | NCOA3_Q1169_1169_1182 | NCOA3_HUMAN | Q9Y6Q9 |
| 61 | QGFLNAQMVAQRSR | NCOA3_Q1232_1228_1241 | NCOA3_HUMAN | Q9Y609 |
| 62 | KTYRGAFQNLFQSVREG | ANDR_FxxLF23_17_32 | ANDR_HUMAN | P10275 |
| 63 | GGETPLFKQFFKNWRDG | GELS_FxxFF389_383_398 | GELS_HUMAN | P06396 |
| 64 | PQAOQKSLLQQLLTEG | NCOA1_LxxLL1435_1427_1441 | NCOA1_HUMAN | Q15788 |
| 65 | SKGQTKLLQLLTTKSDG | NCOA2_LxxLL641_635_650 | NCOA2_HUMAN | Q15596 |
| 66 | KENNALLRYLLDRDDPG | NCOA3_LxxLL738_732_747 | NCOA3_HUMAN | Q9Y609 |
| 67 | RETSEKFKLLFQSYNVG | NCOA4_FxxLF328_322_337 | NCOA4_HUMAN | Q13772 |
| 88 | SLKRRLFRSMFLSTAAG | PAK6_FxxMF261_255_270 | PAK6_HUMAN | Q9N0U5 |
| 69 | TPPPKKFRSLFFGSILG | RAD9A_FxxLF361_355_370 | RAD9A_HUMAN | Q99638 |
| 70 | MMNPLTFKEIFQTTVPG | TRRAP_FxxIF647_641_656 | TRRAP_HUMAN | Q9Y4A5 |
| 71 | KTYRGAFQNFFQSVREG | ANDR_FxxFF23_17_32_L26F | ANOR_HUMAN | P10275 |
| 72 | KTYRGAFQNMFQSVREG | ANDR_FxxMF23_17_32_L26M | ANOR_HUMAN | P10275 |
| 73 | KTYRGAFQNYFQSVREG | ANDR_FxxYF23_17_32_L26Y | ANOR_HUMAN | P10275 |
| 74 | KTYRGALQNLLQSVREG | ANDR_LxxLL23_17_32_F23L_F26L | ANDR_HUMAN | P10275 |
| 75 | GGETPAAKQFFKNWRDG | GELS_AxxFF389_383_398_L388A_F389A | GELS_HUMAN | P06396 |
| 76 | GGETPLFKQAAKNWRDG | GELS_FxxM389_383_398_F391A_F392A | GELS_HUMAN | P06396 |
| 77 | GGETPLFAAFFKNWRDG | GELS_FxxFF389_383_398_K390A_Q391A | GELS_HUMAN | P06396 |
| 78 | GGETPLFKQFFAAWRDG | GELS_FxxFF389_383_398_K393A_N394A | GELS_HUMAN | P06396 |
| 79 | GGEAALFKQFFKNWRDG | GELS_FxxFF389_383_398_T386A_P387A | GELS_HUMAN | P06398 |
| 80 | GGETPLFKQLFKNWRDG | GELS_FXXLF389_383_398_F392L | GELS_HUMAN | P06396 |
| 81 | GGETPLFKQMFKNWRDG | GELS FXXMF389_383_398_F392M | GELS_HUMAN | P06396 |
| 82 | GGETPLFKQYFKNWRDG | GELS_FXXYF389_383_398_F392Y | GELS_HUMAN | P06396 |
| 83 | GGETPLFKQFFKNWRDG | GELS_FxxFF389_383_398_sol | GELS_HUMAN | P06396 |
| 84 | ERKHKILHRLnLQE | NCOA1-derived peptoid A | | |

Example 1

Investigation of the Effect of Estradiol on the Binding Affinity of the Estrogen Receptor (ER) in Interactions with a Variety of Co-Regulator Peptides—Simultaneous Testing of Multiple Co-Regulator Concentrations in one Sample of Nuclear Receptor and Ligand The PamChip® microarray technology was used to generate binding curves of the Estrogen Receptor (ER) interacting with 6 different peptides derived from co-regulator proteins.

Such binding curves are useful to investigate the effect of a ligand or drug (here estradiol was used as example) on the binding affinity of the Estrogen Receptor interaction with co-regulator peptides. Typically, the effect may be measured by two parameters: potency of the ligand and efficacy of the ligand. For accurate determinations of these parameters, the binding profiles need to be measured at different peptide concentrations, at different ligand concentrations, at a single receptor concentration. Such assays proved to be very laborious, time-consuming and reagent consuming when using the known methods in the art, wherein each combination of peptide and ligand concentration is tested consecutively.

With the methods according to the present invention, multiple peptide concentrations are tested in one sample of receptor and ligand at once.

Figure 1:
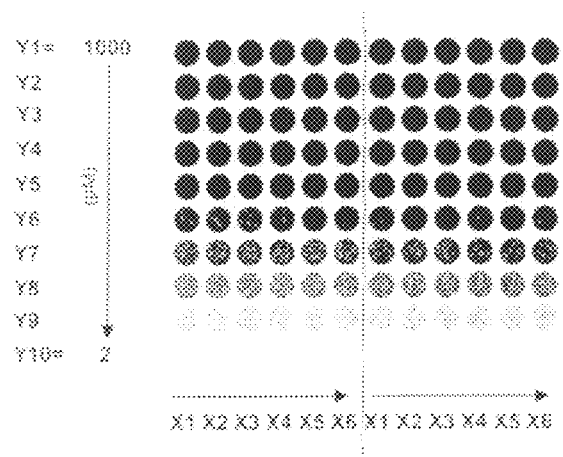
FIG. 1 shows the data related to the investigation as set out in Example 1 of the effect of estradiol on the binding affinity of the Estrogen Receptor (ER) alpha in interactions with a variety of co-regulator peptides.
Figure 1:
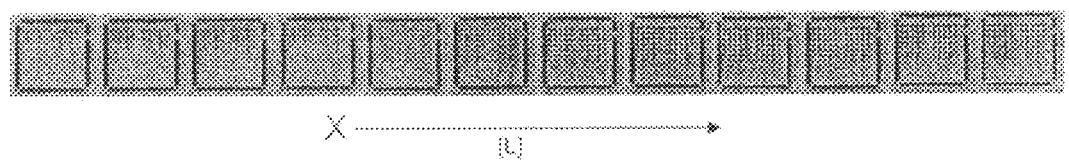
Figure 1:
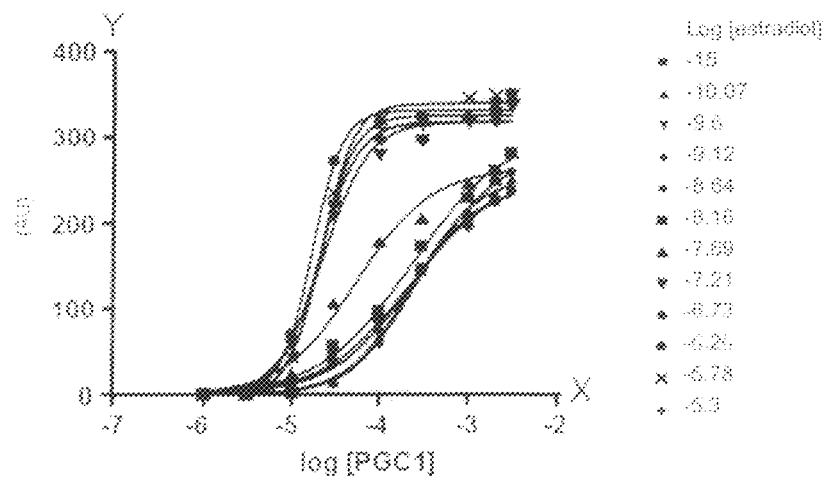

Hereto, as shown in FIG. 1A, a microarray set-up was prepared comprising multiple peptides immobilized at multiple concentrations. A set of 6 co-regulator-derived motifs, X1 to X6, respectively SRC1a-4, SCR1-1, RIP140-8, PGC1a, Dax3, and PPRB (negative control) were immobilized in a range of 10 concentrations Y1 to Y10. The highest concentration was 1000 µM, and two-fold dilutions down to the lowest concentration of 2 µM we used. The amino acid sequences of these peptides are listed in Table 1 (SEQ ID NOs 14, 16, 40, 46, 5 and 45 respectively). A total of two sets of the 6 co-regulator-derived motifs were prepared on a same microarray (see FIG. 1A wherein columns X1 to X6 are repeated) such that each peptide concentration was present twice on the array. The peptides were provided with an N-terminal free cysteine residue and immobilized on the thiol-reactive surface of the PamChip® microarray using methods known in the art.

The peptides, present at different concentrations on the microarray, were incubated with the Estrogen Receptor (ER). The ER protein used comprised only the ligand binding domain (LBD), which binds both the ligand and the peptide and expressed a GST-tag. This tag was used for detection of the ER protein when bound to a peptide on the microarray, by having present in the sample an antibody against this GST-tag, which was fluorescently labeled (anti-GST antibody labeled with Alexa488, Invitrogen). In this experiment the ER and ligand solution was applied to the wells of a PamChip® 96 plate. Each well contained the same microarray as shown in FIG. 1A, and the same ER concentration, but different ligand concentrations. Ligand concentrations increased when going from the outer left column of wells to the outer right column of wells in the PamChip® 96 plate and were the same for each row of wells in the plate. The estradiol was used in concentrations varying from 10E-5.3 molar down to no ligand as indicated in FIG. 1C. It is noted that the absence of ligand, i.e., zero molar, corresponds to a logarithmic value of minus infinite and is indicated for representation purposes as 10E-15 molar. Each sample was incubated by pumping the sample up and down through the porous microarray. Each experimental run comprised 80 cycles of up and down pumping, 1 cycle per 30 seconds. FIG. 1B shows the result of the assays with the highest concentrations of the peptides (i.e., first row of wells in a PamChip® 96 plate). Fluorescence images were taken at the end of a series of pumping steps (80 cycles, followed by a washing step and a final readout). The higher the intensity of a spot is (representing a single peptide at a single concentration, the more binding of receptor is detected. For all spots, i.e. all 6 different peptides and all 10 different peptide concentrations the spot-intensities (fluorescence) were determined using the image quantification software BioNavigator. To determine the effect of the ligand on the receptor peptide interaction, graphs were made in which the receptor binding was plotted against the peptide concentration. FIG. 1C shows such binding graphs for the peptide derived from the protein PGC1. The multiple binding curves shown are derived from the multiple ligand concentrations assayed. Thus, each single curve is derived from data generated in one single well, thus one single microarray, thus one single sample comprising ER and ligand (at a single concentration). Each binding curve is characteristic for the receptor peptide interaction under the conditions of that particular ligand concentration. The data show that when the concentration of the ligand is increased, the binding curve changes and shifts left on the X-axis. This left shift is indicative for the increased affinity of the receptor for the peptide. The degree of left shift is a measurement for the efficacy. The amount of ligand needed for a left-shift is indicative for the potency.

The affinity is determined from the data of a single well incubation by determining in the binding curve the peptide-concentration at which 50% of maximal binding is obtained. This is the Kd. The efficacy is expressed as the ration of the Kd in the presence of saturating concentrations of ligand and the Kd in the absence of ligand. This ratio is referred to as modulation index ($\alpha_{Kd}$). This index is derived from plots like shown in FIG. 1C. In the present microarray-based method the $\alpha_{Kd}$ is determined from only two binding curves, the most left and most right (saturating ligand concentration and no ligand respectively) curve. In other words this $\alpha_{Kd}$ is derived from data from just two microarray incubations, thus two samples.

In conclusion, when looking at alternative methods known in the art, these determine the modulation index from the ratio of induced binding (binding level at saturating ligand concentration divided by control level, i.e. no compound, often referred to as estimated modulation index, ($\alpha_{Est}$) at a single fixed peptide concentration. Such a method is far less preferred over the methods according to the present invention, because it is less able to find differences between compounds E.g. if a peptide concentration too high or too low is taken no modulation of binding can be observed. As such, when the present experiment would have been performed with the above-mentioned method known in the art, choosing a single predetermined peptide concentration of 1E-6, then a different $\alpha_{Est}$ would be determined, than when 1E-7 would have been chosen as predetermined peptide concentration. The compound effect that would be found, in this way, would have been regarded as absent or very low at a predetermined peptide concentration of 1E-6, while the method according to the present invention, based on multiple peptide concentrations, clearly allows the observation and determination of an affinity increasing effect induced by the ligand. The methods according to the present invention also enhance discriminative power between high-affinity ligands which can be discriminated using the Kd derived from the peptide concentration range instead of using a predetermined (high) peptide concentration at which the effect of all compared ligands is has reached saturation and therefore appears identical.

Example 2

Determination of Ligand Potency and Efficacy of a PPAR Gamma Ligand in the Interaction of PPAR Gamma with 53 Different Co-Regulator Derived Peptides The PamChip® microarray technology was used to generate simultaneously efficacy and potency values of a PPAR gamma ligand GW1929 (Sigma Aldrich) modulating the interactions of PPARG-LBD with 53 different co-regulator derived peptide motives. This generates, for the compound of interest, a potency profile as well as an efficacy profile. Such two-parameter profiles are useful both to characterize nuclear receptor ligands and to compare the ligands based on the differences and similarities in their effect on binding of the receptor to different motives (see also Example 6).

As mentioned in Example 1, a ligand is typically characterized by two parameters: potency of the ligand and efficacy of the ligand. For accurate determinations of these parameters, the binding profiles need to be measured at different peptide-concentrations, at different ligand concentrations, at a single receptor concentration. An alternative approach is a measurement involving less peptide concentrations but more peptides at once. In the present example we used only a single peptide concentration, but 53 (instead of 6 in Example 1) different peptides.

Again, the experiment was run using different ligand concentrations, at a single receptor concentration. When using the known methods in the art, such assays would be too laborious, time-consuming and reagent-consuming, wherein each combination of peptide and ligand concentration would be tested consecutively. With the methods according to the present invention, multiple different peptides are tested in one sample of receptor and ligand at once.

Figure 2:
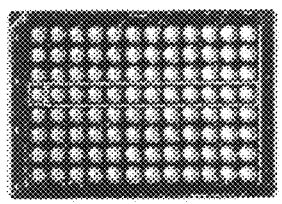
FIG. 2 shows the simultaneous determination of ligand potency and efficacy as set out in Example 2 of a PPAR gamma ligand in the interaction of PPAR gamma with 48 different co-regulator derived peptides (SEQ ID NOs 1, 3-13, 1546, 50-53).
Figure 2:
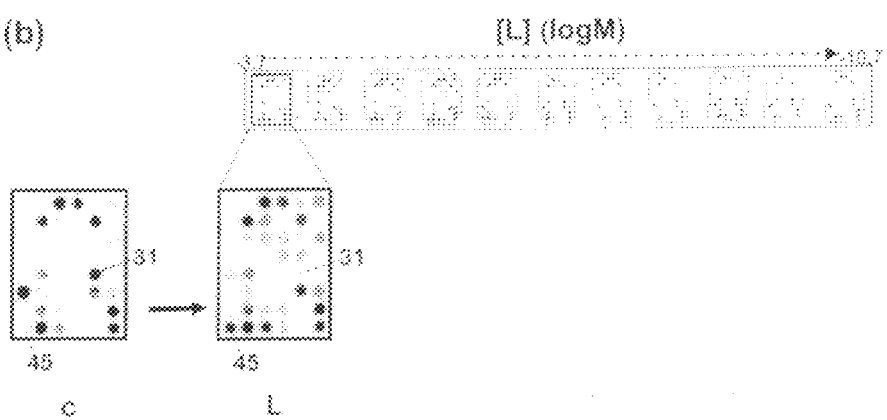
Figure 2:
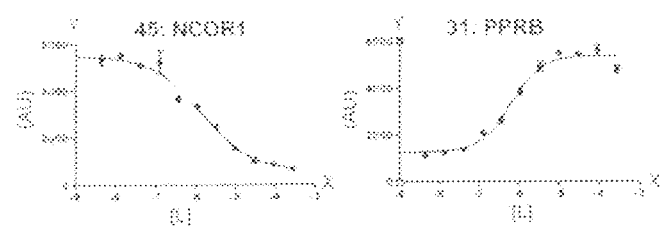
Figure 2:
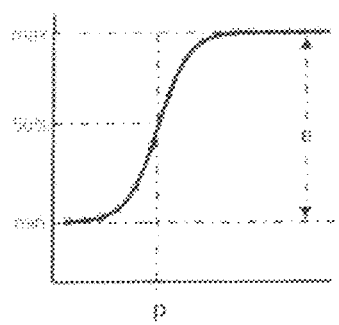

A microarray set-up was prepared comprising 48 peptides immobilized, i.e., a set of 48 co-regulator-derived motifs corresponding to SEQ ID NOs 1, 3-13, 15-46, and 50-53. In this experiment each peptide was present once on the array and at a single peptide concentration (1E-1 M spotting concentration). Preparation of these chips was as described in Example 1. Twelve wells of a 96 well plate (FIG. 2A(a)), each well comprising the same peptide microarray, were incubated with GST-tagged PPAR gamma LBD domain (Invitrogen), and 11 different concentrations of ligand and 1 control (absence of ligand). The ligand used here was GW1929 (Sigma Aldrich), and the concentration series used ranged from 1E-3.7 M down to 1E-10.7 M, using two-fold dilutions as indicated in FIG. 2A(b). The control incubation contained no ligand. The assay was performed according to the method described in Example 1.

FIG. 2A(b) represents the top view of a row of wells in a 96-well plate (FIG. 2A(a)), showing the fluorescence results obtained for the PAR gamma interaction, induced by GW1929, with a the 48 peptide motives. A magnification is shown of the fluorescence image of the microarray incubated with the highest concentration (1E-3.7 M) of GW1929. When compared to the magnified image of the array incubated without GW1929 (only PPAR gamma) some peptides motifs show increase binding, like peptide 45 (SEQ ID NO. 45), while others decreased binding, like peptide 31 (SEQ ID NO. 31), induced by GW1929. This ligand is namely known as a PPAR gamma antagonist, as is apparent from the data obtained from peptide 31 (SEQ ID NO. 31), showing at least decrease of binding of PPAR gamma to this peptide derived from NCOR1, a repressor protein. However, when the effect of GW1929 is read out on peptide 45 (SEQ ID NO. 45), derived from PPRB (PPAR binding protein), this ligand is characterized as a binding agonist. Subsequently, such binding curves were generated for all other peptides, and the parameters for potency (EC50 values) and efficacy (delta) were derived from these curves. FIG. 2B shows how these EC50 and delta values were derived. Curve fitting software (Prism, GraphPad Software Inc.) was used for determination of the maximum and minimum binding level. Based on these levels the software calculated the difference between the top and bottom plateau of the sigmoidal binding curve (delta) and the concentration of ligand where 50% of binding is observed (EC50). It should be noted that the parameter for efficacy is different in this approach from the modulation index ($\alpha_{Kd}$), used in the approach using multiple peptide concentrations described in Example 1. These simultaneously derived potency and efficacy parameters, derived for all 48 peptides, are shown in FIG. 3. This figure shows the potency (upper panel) data, expressed as EC50 (log M) values, as well as the efficacy data, expressed as delta values (increase fluorescence intensities) derived in this single assay experiment. As said, for all peptides an EC50 value could be determined, but in FIG. 3 only the values that could be determined accurately (regression coefficient of the fit better than 0.7) are represented.

The availability of two parameters at once proved to improve both ligand characterization and ligand comparisons. Regarding ligand characterization, this information allows to understand how ligand binding influences the capabilities of the receptor to bind co-regulator proteins. This mechanistic information is useful in the prediction of a compound effect in a cell. E.g. if a certain compound generates identical potency values for two peptide motifs (e.g. peptide 4 and 40, DAX1 and NRIP, respectively) it may indicate that identical ligand effects can be expected for both co-regulator proteins. In case the efficacy values would be similar as well, this may indicate that both effects could be equally involved. However, if the efficacy values are different, as is the case in the present example for peptides 4 and 40 (SEQ ID NOs 4 and 40), this also means that different effects of receptor binding to these two co-regulator proteins may be expected (CBP and DAX1 respectively), although the same amounts of ligand are needed to accomplish this (same potency). For the same reasons mentioned above, the comparison of compounds is improved by using two instead of one parameter, as well.

Example 3

Kinetics of Binding of the Glucocorticoid Receptor (GR) in Interactions with a Variety of Co-Regulator Peptides—Testing of Multiple Assay Time Points, and Multiple Co-Regulator Derived Peptides in One Sample of Nuclear Receptor and Ligand The PamChip® microarray technology was used to generate time curves of ligand-induced binding of the glucocorticoid receptor (GR). The ligand of interest was dexamethasone. Such time curves are useful to investigate the effect a ligand or drug on the kinetics of binding of the nuclear receptor with co-regulator peptides. Additionally, time-curves improve the accuracy and statistics of the measurement. Moreover, kinetic measurements improve the power to discriminate interactions with different peptides.

For accurate determinations of kinetic parameters, time curves need to be generated, and for multiple peptide motifs.

Therefore binding need to be measured at multiple different time points using multiple different peptide motifs, both in the presence and absence of a ligand. Such assays proved to be very laborious, time-consuming and reagent consuming when using the known methods in the art, wherein each combination of peptide and time point is tested consecutively and using different samples. The methods according to the present invention allow testing of time curves of multiple peptides in one single sample, which reduces experimental variances, and makes comparison of different peptide binding kinetics easier.

A microarray set-up was prepared comprising 53 peptides immobilized (SEQ ID NOs 1 to 53 as listed in Table 1). The microarray was prepared in the same way as described in the examples above, each peptide was present once on each array and applied at a single concentration of 1E-3 M. Two wells of a PamChip96 microtiter plate were incubated with GST-tagged glucocorticoid receptor LBD domain (Invitrogen) in the absence (control) and presence of ligand (dexamethasone, 1E-6.3 M). FIG. 4 shows the resulting time curves of binding. The sample was applied to the microarray at the time point of 20 cycles. Only three of the 53 time curves generated from one sample are shown. While the kinetics of binding are highest for peptide 1 (CBP, SEQ ID NO. 1) in the absence of ligand (control) in comparison to peptide 7 and 14 (SEQ ID NOs 7 and 14), the kinetics of this peptide 1 are lowest in the presence of the ligand dexamethasone. Furthermore, the results demonstrate the increased discriminating power of using time curves. In the presence of ligand (right panel FIG. 4) the degree of binding at the single time points of 31 cycles is very similar for peptide 1 and 7. Thus based on a single time point the effect of the ligand would be regarded identical for both the interaction of GR with CBP derived motif (SEQ ID NO. 1) and the DAX1 derived motif (SEQ ID NO. 7). However, the additional data points generated at multiple additional time points enabled by this method, clearly show the different kinetic responses of these motifs. The optimal time point allowing best discrimination of motif responses is in this example early, but can be also late (data not shown). While other single time point methods known in the art require optimization of the time point, in essence for every peptide and possibly for every ligand, which is very time consuming, not practical and therefore mostly omitted, such optimization is not needed in the methods of the present invention.

The increased discriminatory power, enabled by the time curves, of the peptide motifs is useful in applications like ligand classification and mechanism of action studies.

Example 4

Binding Profiles from Crude Cell Extracts from Estrogen Receptor Alpha-Transfectants The PamChip® microarray technology was used to generate profiles of ligand-induced binding of estrogen receptor alpha (ERα) in a crude extract of an ERα-transfected cell line. The (ERα) ligands of interest were estrogen and tamoxifen to investigate whether (ERα) could be modulated in a cellular context.

The use of crude extracts, versus purified NR protein, in investigating ligand-induced binding of nuclear receptors to co-regulator derived motifs, is useful for multiple, practical, economical, biological and pharmaceutical reasons:
  no need for cumbersome purification (practical and economical reason);
  constructs that can not be purified, or that lose functionality upon purification can be tested (e.g. full length NHR constructs are known to be hard to study as full length proteins when purified);
  easy testing of mutant forms of NHRs; and
  the ligands, compounds and drugs are investigated in a cell based assay, which is an environment much more resembling endogenous conditions than an assay using purified proteins. In this way, for example, cellular drug effects can be measured (biological and pharmaceutical reasons).

In such cell based measurements, it is very useful and informative to investigate the cellular effect of a ligand on the binding capacity of the receptor of interest, with many co-regulator peptides. Such assays prove to be limited for reasons of the crude extract being to complex for accurate detection of NR mediated interactions. So called bead-based methods, for example, tend to suffer from bead aggregation, possibly caused by protein mediated interactions of beads. The methods according to the present invention allow using crude extracts and investigating in one single assay the effect of a ligand on the NR binding to multiple motifs.

A microarray set-up was prepared comprising 53 immobilized peptides (SEQ ID NOs 1 to 53) as described above in Example 3. The experimental setup is shown in FIG. 5. A cell line (U2OS) was transfected with an ER alpha DNA construct (0.4 µg, pcDNA3-YFP-ERa-GFP) enabling expression of the full length ER alpha as a GFP-tagged fusion protein. The transiently transfected cells were used in a number of culturing experiments in which the cells were treated for 8 hours with tamoxifen (1E-7 M), estradiol (1E-7) or in the absence of ligand (control). Cells were harvested and lysed using MPER lysis buffer (Pierce) in the presence of HALT protease inhibitor cocktail (Pierce) and HALT phosphatase inhibitor cocktail (Pierce). The crude extracts (cell lysates) were incubated on the microarrays in the presence of two antibodies for detection of the ER full length protein binding to the peptide motifs: fluorescently labeled anti rabbit (Santa Cruz), and a rabbit anti GFP antibody (NKI). The microarray incubation method was identical to the methods described in the examples above (kinetic measurement). The right panel of FIG. 5 shows the resulting fluorescent images after a final washing step. Compared to the control experiment, estradiol enhances binding of the full length ERα protein to multiple peptide motifs, as apparent from higher intensities of the spots. Tamoxifen, known as a ERα antagonist attenuates binding of the receptor, as apparent from decreased intensity of the spots compared to control.

The data show that the methods of the present invention allow the measurement of binding profiles of a nuclear receptor expressed in cells and present in a crude cell extract. Furthermore, the data show that the effect of ligands like the agonist estradiol and the antagonist tamoxifen can be measured. This allows characterization of ligands in a cellular context.

Example 5

Different Modulations of Multiple Different Nuclear Receptor-Coregulator Interactions by Multiple Different Ligands (of Various Classes) or Other Agents—Investigating the Scope of the Application of the Method of the Present Invention The PamChip® microarray technology was used to generate ligand or by other agents induced binding profiles from multiple different nuclear receptors. If a broad range of receptors and ligand and agents can be profiled, then the methods according to the invention for simultaneous determination of ligand efficacy and potency (see e.g., Examples 1 and 2) can be applied broadly as well.

Hereto, different nuclear receptors were profiled in the absence or presence of ligand or other agents. These ligand and agents were selected from a variety of compound classes as indicated below. The results are shown in FIG. 6. The following combinations were tested:

A, estrogen receptor alpha (ERα) modulation by the estrogen estradiol (class of steroids);

B, progesteron receptor (PR) by progesterone (class of steroids);

C, glucocorticoid receptor (GR) by dexamethasone (class of corticosteroids);

D, peroxisome proliferator-activated receptor gamma (PPARγ) by rosiglitasone (class of the thiazolidenedione);

E, liver x receptor beta (LXRβ) by 22[R]hydroxy cholesterol (class of hydroxysterols);

F, androgen receptor (AR) by dihydroxytestosterone and a gelsolin derived peptide (class of steroids and peptides, respectively);

G, androgen receptor (AR) by a NCOA1-derived peptoid A (class of peptidomimitics); and H, estradiol treated estrogen receptor alpha by cAMP-induced PKA (kinase) (class of enzymes and nucleotides).

The ER, PR, GR and LxRβ were tested as purified LBD-GST fusion proteins (Invitrogen). The ligands and agents estradiol, progesterone, dexamethasone, cAMP (Sigma Aldrich), and rosiglitasone (Alexis) are commercially available. Gelsolin derived peptide (SEQ ID NO. 83) and NCOA1-derived peptoid A (H-ERKHKILHRLnLQE-NH2) (SEQ ID NO. 84) were kindly provided by the Utrecht University, synthesized according to published protocols and methods known in the art. The microarray incubation experiment was performed as mentioned in Example 1.

The AR (LBD-His construct) and ER (full length GFP construct) transfectants were tested as crude cell extracts from cells transfected with AR and ER expressing DNA constructs. The ER construct was described in Example 4. The AR LBD-his fusion protein was derived from baculovirus-infected insect cells. Crude extracts were partially purified using his-tag affinity columns and dialysis. The ER construct was prepared as described in Example 4 for the ER constructs, with the exception that 16 hours after transfection cells were treated with estradiol, and subsequently treated with cAMP for 8 hours.

FIG. 6 shows the resulting binding profiles obtained. For all receptors tested a ligand or agent induced binding profile was obtained. All profiles were different, indicative of the many different modes of induced binding of different nuclear receptors that can be studied by the methods according to the present invention.

Example 6

Investigation of the Binding Profiles of Nuclear Hormone Receptors to Peptide Motifs to non-LxxLL Motifs—FxxLF and Q-Rich Domains The PamChip® microarray technology was used to investigate binding to non LxxLL motives. LxxLL motives are typical NR-box motifs. With the present experiment it was investigated if the method of the present invention could be applied as well to FxxFF and FxxLF motifs and variants thereof, and glutamine-rich (Q-rich) domains. This is useful to uncover features of these non-LxxLL motifs and O-rich domains. The use of these motifs and domains would further broaden the scope of application of the methods according to the invention for simultaneous determination of ligand efficacy and potency (see e.g., Examples 1 and 2).

Binding profiles were generated of AR-LBD and full length ERα induced by dihydroxytestosterone (DHT) and a combination of estradiol and cAMP, respectively. Experimental conditions were used as described above in Example 5 for transfected AR-LBD and full length ERα. A microarray was prepared comprising the peptides indicated in FIGS. 7 and 8. Sequences of these peptides are listed in Table 1. FIG. 7A shows the DHT induced binding of AR-LBD to wild type motifs complying to the consensus motif LxxLL (e.g. peptide 66, derived from NCOA2) as well as other motives like FxxFF (SEQ ID NO. 63), FxxLF (SEQ ID NO. 67), and FxxMF (SEQ ID NO. 68). The different levels of binding observed are indicative for the preferred motifs: the gelsolin derived motif is a preferred binding partner for AR-LBD over the NCOA4 derived motif. FIGS. 7B and C show the DHT induced binding of AR-LBD to wild type motifs of androgen receptor and gelsolin respectively. The results of this mutation analysis provide useful information on which amino acid residue is important in the binding interaction and which are not. FIG. 8 shows the estradiol and cAMP induced binding of full length ERα Q-rich domains. Using the methods of the present invention ligand-induced profiles can be performed based on motifs from mutated proteins, and so called Q-rich domains as well.

The invention claimed is:

1. A method for measuring compound efficacy and potency on nuclear receptor-co-regulator interaction, comprising the following steps:
   (i) co-incubating at least one nuclear receptor and at least one compound under conditions that allow interaction;
   (ii) co-incubating the nuclear receptor-compound mixture of step (i) with a variety of different co-regulator peptides, under conditions that allow compound modulated receptor-co-regulator interaction;
   (iii) determination of compound modulated receptor-co-regulator interaction as a function of co-regulator concentration;
   (iv) determination of compound modulated receptor-co-regulator interaction as a function of compound concentration;
   wherein said different co-regulator peptides are immobilized onto a solid support in the format of a microarray having each unique peptide sequence coupled onto a distinct spot on said solid support.

2. Method according to claim 1, wherein said nuclear receptor is selected from the group consisting of receptors for glucocorticoids (GRs), androgens (ARs), mineral corticoids (MRs), progestins (PRs), estrogens (ERs), thyroid hormones (TRs), vitamin D (VDRs), retinoids (RARs and RXRs), steroids, peroxisomes (XPARs and PPARs) and icosanoids (IRs) and orphan receptors.

3. Method according to claim 1, wherein said compound is selected from the group consisting of peptides, peptoids, biogenic amines, amino acids, ions, lipids, nucleotides, enzymes, vitamins and hormones.

4. Method according to claim 3, wherein said compound is selected from the group consisting of androgens, corticosteroids, estrogens, prostanoids, farnesoids, progesterone, vitamins A and D, thyroid hormone, retinoic acid, fatty acids, prostaglandin, cholesterol, oxysterols, bile acids, and testosterone.

5. Method according to claim 1, wherein said microarray of co-regulators comprises various co-regulators with various concentrations per co-regulator.

6. Method according to claim 1, wherein said co-regulators are co-activators and/or co-repressors, including fragments thereof, containing a binding domain for the nuclear receptor.

7. Method according to claim 1, wherein said co-regulator peptides comprise the amino acid core consensus sequence chosen from the group consisting of LxxLL, LxxML, FxxFF and LxxIL.

8. Method according to claim 1, wherein duplicates of said microarray are imbedded in a multi-well plate.

9. Method according to claim 1, wherein said microarray is a flow-through microarray.

10. Method according to claim 1, wherein a binding profile for the compound is determined.

11. Method according to claim 1, wherein compound potency and efficacy are concomitantly determined.

12. Method according to claim 1, wherein said co-regulator peptides are co-regulator peptides according to SEQ ID NOs 1 to 84.

* * * * *